United States Patent
Spero

(10) Patent No.: US 11,648,062 B2
(45) Date of Patent: May 16, 2023

(54) SYSTEM FOR CONTROLLING ABLATION TREATMENT AND VISUALIZATION

(71) Applicant: Acessa Health Inc., Austin, TX (US)

(72) Inventor: Richard Spero, Austin, TX (US)

(73) Assignee: Acessa Health Inc., Austin, TX (US)

( * ) Notice: Subject to any disclaimer, the term of this patent is extended or adjusted under 35 U.S.C. 154(b) by 750 days.

(21) Appl. No.: 16/186,215

(22) Filed: Nov. 9, 2018

(65) Prior Publication Data

US 2019/0133696 A1 May 9, 2019

Related U.S. Application Data

(60) Provisional application No. 62/583,972, filed on Nov. 9, 2017.

(51) Int. Cl.
*A61B 34/20* (2016.01)
*A61B 8/12* (2006.01)
(Continued)

(52) U.S. Cl.
CPC ............ *A61B 34/20* (2016.02); *A61B 8/0841* (2013.01); *A61B 8/12* (2013.01); *A61B 8/4416* (2013.01);
(Continued)

(58) Field of Classification Search
CPC ........ A61B 2018/1475; A61B 18/1477; A61B 2018/00577; A61B 2018/00583;
(Continued)

(56) References Cited

U.S. PATENT DOCUMENTS 5,827,276 A 10/1998 Leveen et al.
5,855,566 A 1/1999 Dunlap et al.
(Continued)

FOREIGN PATENT DOCUMENTS

JP H11-509431 8/1999
JP 2017-94084 6/2017
(Continued)

OTHER PUBLICATIONS

Bergamini, MD. et al. "Laparoscopic radiofrequency thermal ablation: A new approach to symptomatic uterine myomas," American Journal of Obstetrics and Gynecology, 192:768-73 Varese, Italy, Mar. 1, 2005.
(Continued)

*Primary Examiner* — Carolyn A Pehlke
(74) *Attorney, Agent, or Firm* — Vista IP Law Group, LLP

(57) ABSTRACT

A system for controlling ablation treatment and visualization is disclosed where the system comprises a tissue ablation instrument having one or more deployable stylets and a first electromagnetic sensor and an ultrasound imaging instrument which may be configured to generate an ultrasound imaging plane and further having a second electromagnetic sensor. An electromagnetic field generator may also be included which is configured for placement in proximity to a patient body and which is further configured to generate an output indicative of a position the first and second electromagnetic sensors relative to one another. Also included is a console in communication with the ablation instrument, ultrasound imaging instrument, and electromagnetic field generator, wherein the console is configured to generate a representative image of the tissue ablation instrument oriented relative to the ultrasound imaging plane and an ablation border or cage based upon a deployment position of the one or more stylets.

26 Claims, 16 Drawing Sheets

(51) Int. Cl.
| | |
|---|---|
| *A61B 18/04* | (2006.01) |
| *A61B 8/00* | (2006.01) |
| *A61B 18/02* | (2006.01) |
| *A61B 18/14* | (2006.01) |
| *A61B 8/08* | (2006.01) |
| *A61B 90/00* | (2016.01) |
| *A61B 34/00* | (2016.01) |
| *A61M 25/00* | (2006.01) |
| *A61B 17/00* | (2006.01) |
| *A61B 18/00* | (2006.01) |

(52) U.S. Cl.
CPC .............. *A61B 8/463* (2013.01); *A61B 8/465* (2013.01); *A61B 8/466* (2013.01); *A61B 8/469* (2013.01); *A61B 18/042* (2013.01); *A61B 18/1477* (2013.01); *A61B 18/1485* (2013.01); *A61B 34/25* (2016.02); *A61B 90/361* (2016.02); *A61B 2017/00199* (2013.01); *A61B 2018/00559* (2013.01); *A61B 2018/00577* (2013.01); *A61B 2018/00791* (2013.01); *A61B 2018/00904* (2013.01); *A61B 2018/0212* (2013.01); *A61B 2018/143* (2013.01); *A61B 2034/2051* (2016.02); *A61B 2034/2063* (2016.02); *A61B 2034/2072* (2016.02); *A61B 2090/365* (2016.02); *A61B 2090/378* (2016.02); *A61B 2090/3979* (2016.02); *A61M 2025/0096* (2013.01)

(58) Field of Classification Search
CPC .......... A61B 2018/00559; A61B 18/18; A61B 34/20; A61B 34/10; A61B 2018/00702; A61B 2018/00696; A61B 2018/00714; A61B 2018/00738; A61B 18/00; A61B 18/14; A61B 2018/00005; A61B 2018/00315; A61B 8/4254
See application file for complete search history.

(56) References Cited

U.S. PATENT DOCUMENTS

| | | | |
|---|---|---|---|
| 6,241,725 | B1 | 6/2001 | Cosman |
| 6,454,765 | B1 | 9/2002 | Leveen et al. |
| 6,840,935 | B2 | 1/2005 | Lee |
| 7,678,106 | B2 | 3/2010 | Lee |
| 8,080,009 | B2 | 12/2011 | Lee et al. |
| 8,241,276 | B2 | 8/2012 | Epstein et al. |
| 8,251,991 | B2 | 8/2012 | Epstein et al. |
| 8,262,574 | B2 * | 9/2012 | Placek ............... A61B 18/1477 600/443 |
| 8,512,330 | B2 | 8/2013 | Epstein et al. |
| 8,512,333 | B2 | 8/2013 | Epstein et al. |
| 9,510,898 | B2 | 12/2016 | Epstein et al. |
| 9,662,166 | B2 | 5/2017 | Lee et al. |
| 9,861,426 | B2 | 1/2018 | Epstein et al. |
| 10,548,666 | B2 | 2/2020 | Girotto et al. |
| 2006/0200121 | A1 | 9/2006 | Mowery |
| 2011/0137156 | A1* | 6/2011 | Razzaque ............. A61B 34/20 600/424 |
| 2011/0230874 | A1* | 9/2011 | Epstein ............... A61B 18/1477 606/41 |
| 2012/0245575 | A1 | 9/2012 | Epstein et al. |
| 2012/0245576 | A1 | 9/2012 | Epstein et al. |
| 2014/0276052 | A1 | 9/2014 | Rankin et al. |
| 2015/0190206 | A1 | 7/2015 | Epstein et al. |
| 2016/0095537 | A1 | 4/2016 | Epstein |
| 2016/0128669 | A1* | 5/2016 | Hill ........................ A61B 8/085 600/424 |
| 2017/0079615 | A1 | 3/2017 | Burnside et al. |
| 2017/0079681 | A1 | 3/2017 | Burnside et al. |
| 2017/0135760 | A1* | 5/2017 | Girotto ................. A61B 34/10 |
| 2018/0132927 | A1* | 5/2018 | Chen ................. A61B 18/1815 |

FOREIGN PATENT DOCUMENTS

| | | |
|---|---|---|
| WO | WO 2013/102072 | 7/2013 |
| WO | WO 2019/094808 | 5/2019 |

OTHER PUBLICATIONS

Foreign OA for JP Patent Appln. No. 2020-525873 dated Oct. 24, 2022 (with English translation).

Non-Final Office Action for U.S. Appl. No. 17/135,203 dated Jan. 26, 2023.

Office Action dated Feb. 21, 2023 for Chinese Patent Application No. 2018800723064, (9 pages).

Translation of Office Action dated Feb. 21, 2023 for Chinese Patent Application No. 2018800723064 provided by AFD China Intellectual Property Law Office (Agent) on Mar. 21, 2023 (6 pages).

* cited by examiner

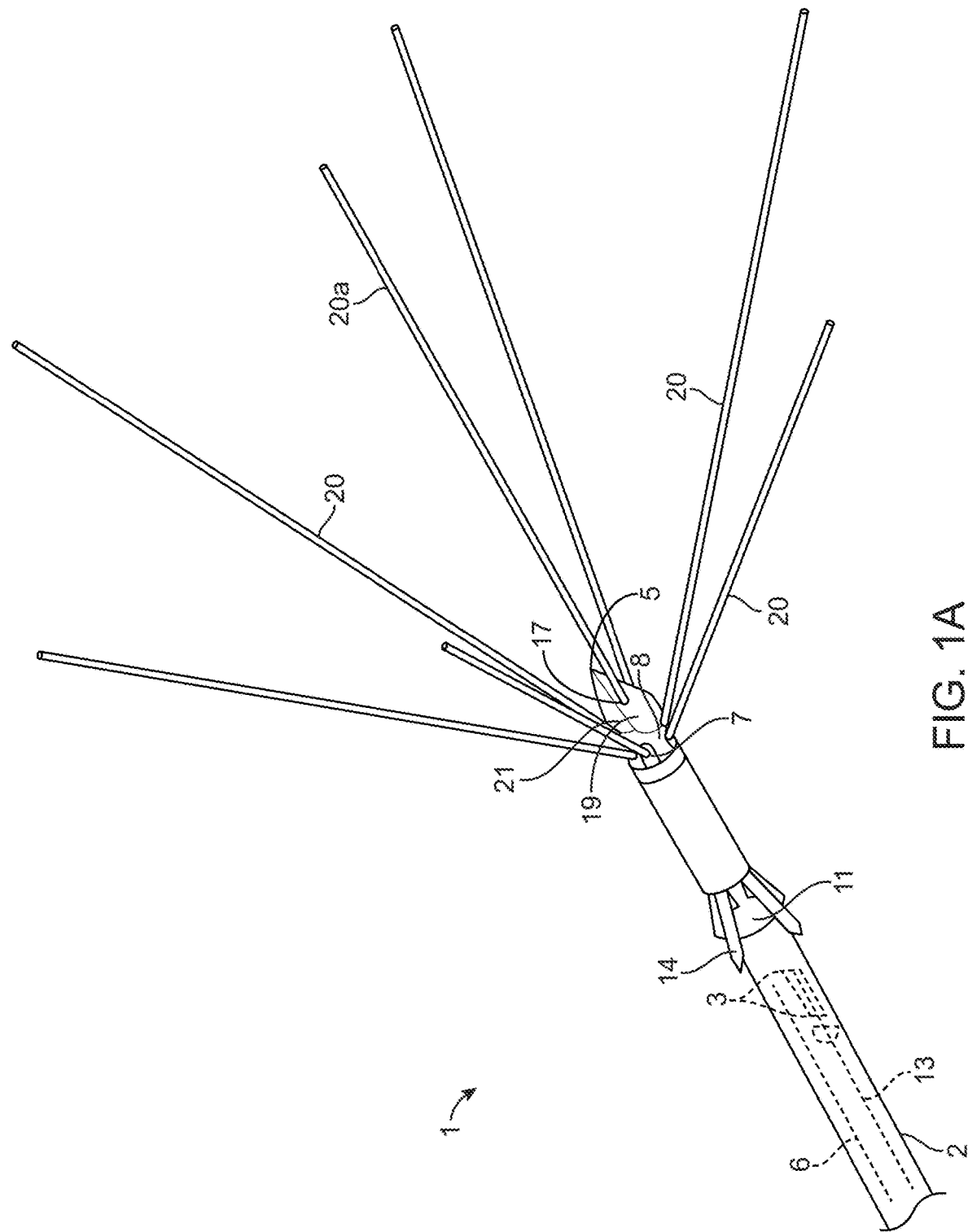

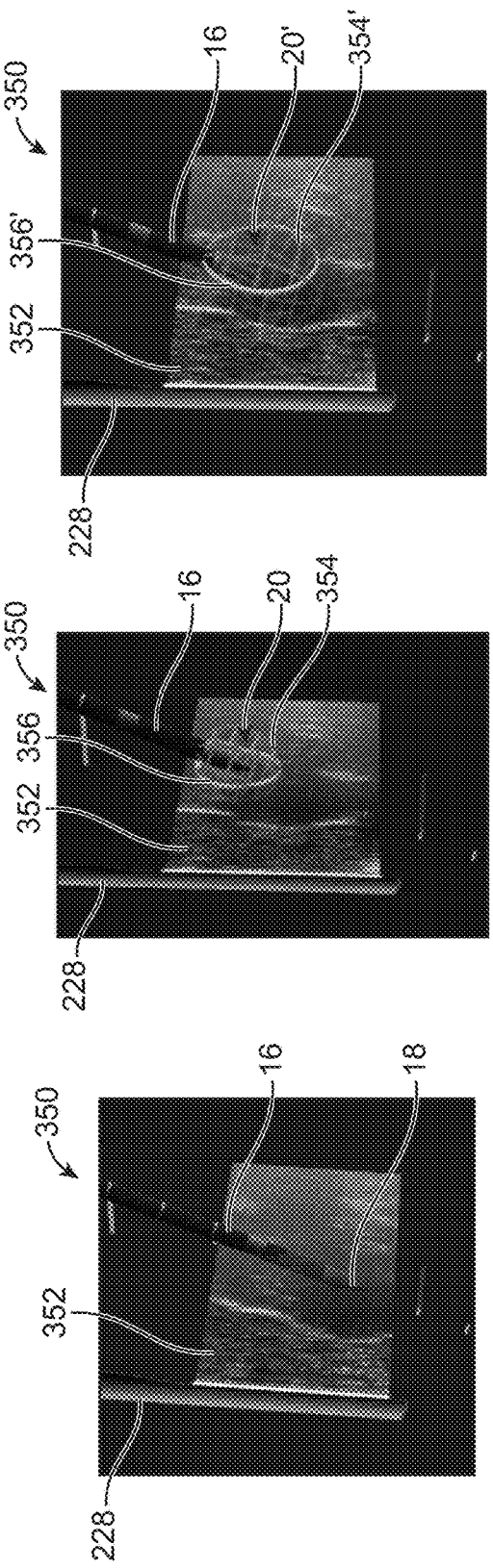
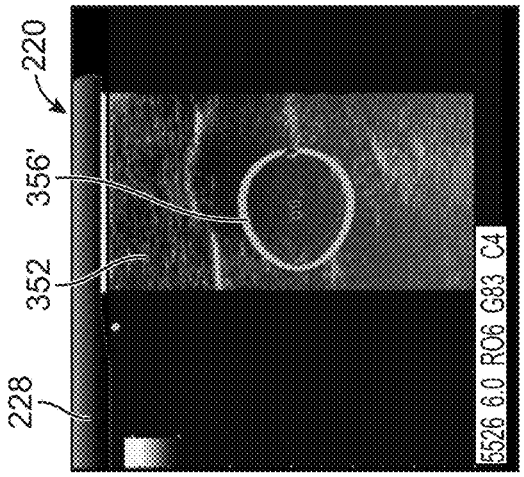
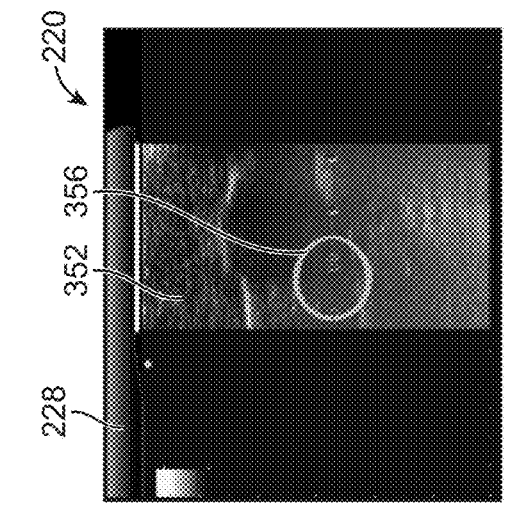
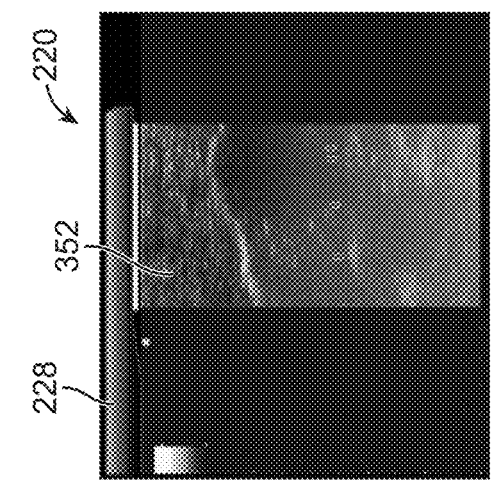
FIG. 9A  FIG. 9B  FIG. 9C
FIG. 10A  FIG. 10B  FIG. 10C

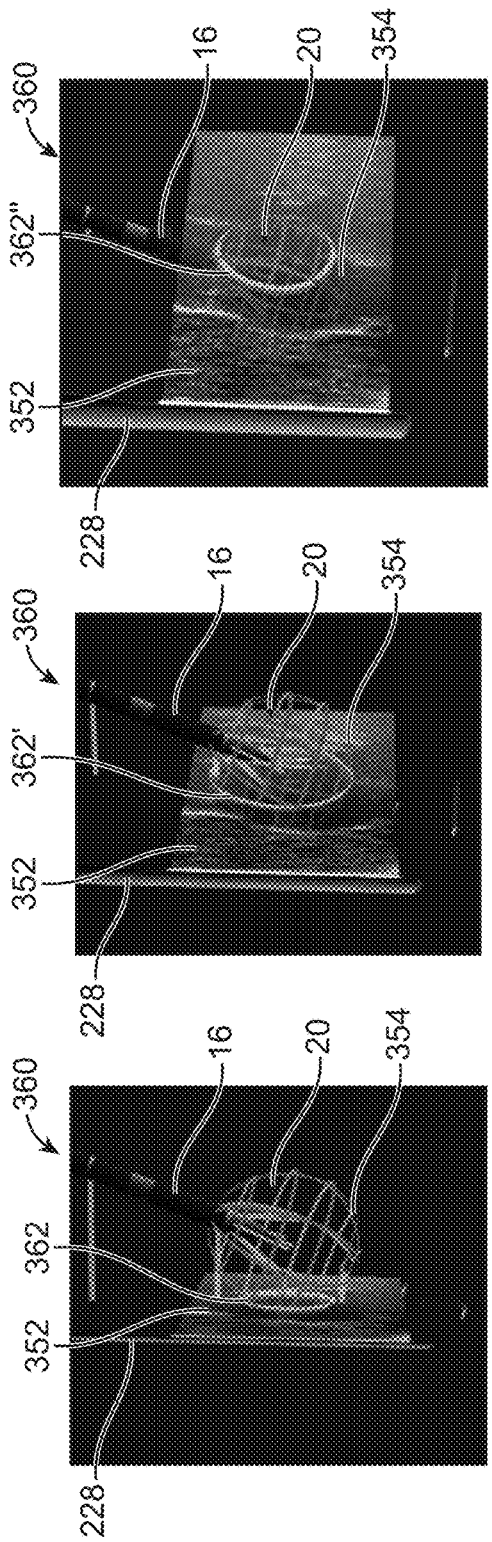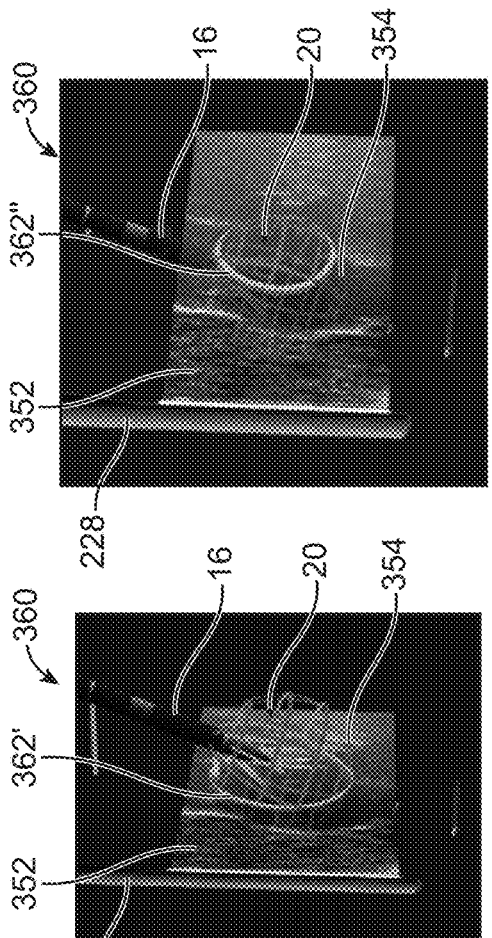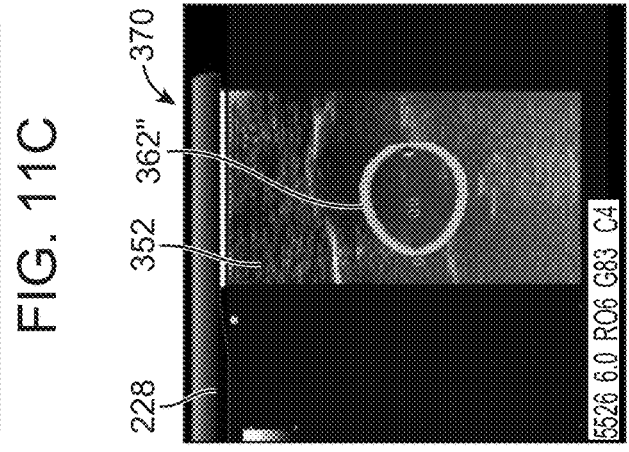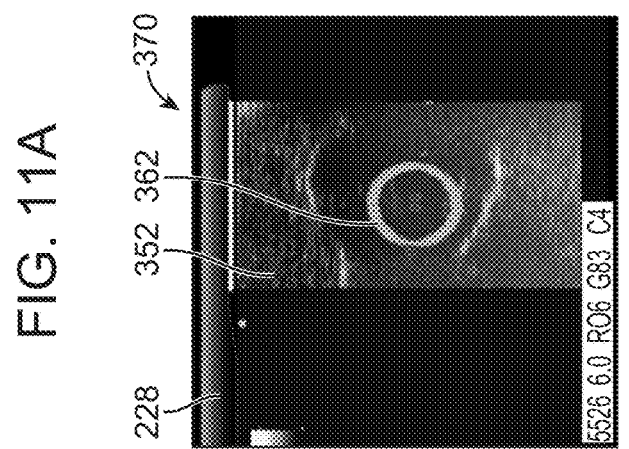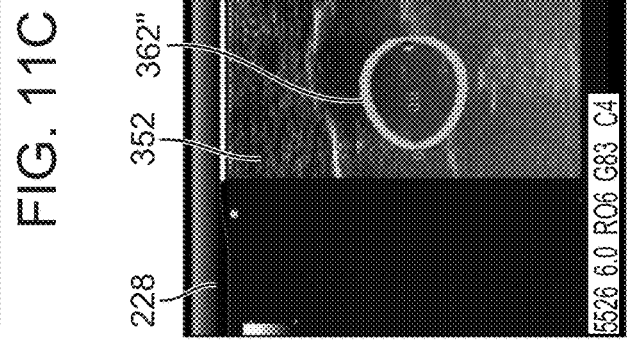
FIG. 11A  FIG. 11B  FIG. 11C
FIG. 12A  FIG. 12B  FIG. 12C

SYSTEM FOR CONTROLLING ABLATION TREATMENT AND VISUALIZATION

CROSS-REFERENCE TO RELATED APPLICATIONS

This application claims the benefit of priority to U.S. Prov. App. 62/583,972 filed Nov. 9, 2017, which is incorporated herein by reference in its entirety.

FIELD OF THE INVENTION

The invention relates to control mechanisms for a medical device positioned in a patient's body for ablation of a tumor, such as a uterine fibroid and, more particularly, to a tissue ablation treatment device which coordinates the energy delivery, imaging, and navigational control in a seamless and cohesive system.

BACKGROUND OF THE INVENTION

Today, surgeons use various forms of imaging to make possible or assist in a wide range of surgical procedures. Imaging allows for more precise operations that reduce collateral damage and shorten recovery time as well as enhance survival rates.

Imaging systems may use a wide range of technologies. These imaging systems are of particular value in the performance of minimally invasive surgical procedures, where the desire to minimize damage to healthy tissue is promoted by minimizing the width of surgical instruments and introducing them into the body through elongated narrow diameter guidance and support members.

For example, surgical macerators may be supported at the end of a cable and sheath mechanical drive system where the cable and sheath serves the additional function of driving and guiding the macerator to the point where the surgery is to be performed. Such a macerator may include a fiber optic bundle with optics for imaging the vicinity of the tissues near the macerator and conveying that image to, for example, a display system with an LCD display for presenting the images to the surgeon, allow him to quickly and reliably operate on the unwanted tissue.

Other approaches involve the introduction of the end of a fiber optic bundle with imaging optics into an existing body cavity or channel, and transmitting the image to the other end of the fiber optic bundle, where it may be received by focusing optics and an image sensor, such as a CCD transducer. Such devices may be of small caliber, for example, narrow enough to enter the nose and be introduced into the throat.

Still another possibility is to create a cavity in the body, for example by insufflating the abdominal cavity. One may then use the cavity as an imaging space allowing an optical camera to inform the surgeon with optically generated images of the position and orientation of the instrument and the anatomical feature being operated upon, thus allowing the surgeon to perform the surgery.

A different dimension of visualization may be achieved through the use of ultrasound imaging. For example, an ultrasound transducer may be positioned against the surface of an organ to generate an image of the interior of the organ. Such imaging may be used to show anatomical features inside the organ and the position of instruments, such as an ablation probe.

Such systems are of particular value during surgical procedures as they increase the amount of information available to the surgeon during a surgical procedure, such as the ablation of an undesired anatomical artifact, such as a uterine fibroid.

However, such systems typically require the user of multiple components which are separate from one another which may present multiple sources of information in a disparate manner. For instance, imaging systems, navigational mapping systems, tissue ablation systems, etc. may each require its own equipment and attention in utilizing the device and may also present a crowded operating theater. This may lead to confusing results and treatments.

Accordingly, there exists a need for a comprehensive system which can combine multiple sub-systems into cohesive and seamless system for treating tissues within a patient body.

BRIEF SUMMARY OF THE INVENTION

A system is provided which provides a first imaging device of a first type having a first image output which is positioned to image an area being subject to surgery. A second imaging device of a second type has a second image output and is positioned to image the area being subjected to surgery. A computer is coupled to receive the first and second image outputs and merge the first and second image outputs into a unitary image output representing a unitary image. Software, resident in the computer generates a graphic user interface including a menu and submenu items. A surgical device is coupled to the computer. Software, resident in said computer, receives and displays information received from the surgical device and/or controls the operation of the surgical device. A display as coupled to the computer for displaying the graphic user interface and the unitary image.

The inventive ablation device may be controlled by using a simplified button array in conjunction with a graphical user interface ("GUI"). The inventive GUI graphically portrays a uterine ablation probe which allows the physician to visualize the procedure as well as the parameters of each step in the ablation process and results.

The advantage of the inventive GUI-based system over conventional alpha-numeric controls is the ability to visually display the device's operating parameters in an intuitive fashion, together with medical data associated with the particular patient. At the same time, the inventive device provides for an intuitive and simplified means to control the application of ablation energy. In this way, the device is easier to use and configure, and provides the surgeon with a better picture of the procedure and the data relative to the operation of the device.

Accordingly, the system may be composed of different components into a comprehensive overall system which may integrate an RF ablation component, an ultrasound system, and a guidance mapping system. The combination of these components may allow for the user to seamlessly integrate ultrasound and guidance to help position the ablation probe relative to the tissue for treatment. The combination of the various individual components into a seamless system enables for the continuous monitoring, feedback, and accuracy of treatment as the ultrasound probe may communicate and obtain instant feedback to better manage the treatment outcomes. For example, having the ultrasound probe work in conjunction with the guidance system enables the guidance to integrate, interpret, and respond to the ultrasound images in real time.

Accordingly, a single console may be used to integrate each of the different components and computer into an overall coherent system which facilitates the communication between each of the sub-systems. Hence, the RF ablation component may have the ablation probe interact with an electromagnetic field generated by the guidance mapping system to generate ablation probe positional information for spatial tracking. The computer may be responsive to the ultrasound probe positional information and the ablation probe may generate a graphic representation showing the positional relationship between the ultrasound image and the ablation probe to guide placement of the ablation probe into an anatomical location imaged by the ultrasound probe. Hence, in one embodiment, the computer and interface as well as interface and ablation energy source and ultrasound machine may all be integrated into a single console.

The apparatus additionally comprises a display device responsive to the computing device so as to display a graphic representation. The display may comprise a guidance animation displayed on the GUI, which is generated by the computing device, which processes the guidance information. Real-time correctional information can be viewed by a user in the guidance animation.

The guidance system may use the electromagnetic spatial tracking to calculate the position and orientation of sensors within a defined volume. The sensors may accordingly be embedded in the tip of the ablation probe and ultrasound probe or within or along an ultrasound transducer sleeve having the sensors. The computer may determine the position and orientation relative to one another within the patient's abdominal cavity and display representative animated images on a GUI. The acquired ultrasound images may be displayed in a seamless integrated image with the representative animated images.

Given the integration of multiple images and instruments, there may be several configurations for positioning of the display monitors relative to the patient and the practitioner to facilitate a treatment procedure.

Turning now to the console which may integrate each of the different components, one variation of the console may be configured to receive the connections or signals from each of the various components for integrating them into a seamless user interface. The console may be coupled to a monitor such as a hospital-owned accessory monitor for displaying the generated information. A foot pedal (e.g., pneumatic dual-foot pedal) may be coupled to the console and used to selectively active the ablation probe so that RF energy may be turned ON and OFF.

One or more pads (e.g., disposable set of 2 units) may also be coupled via a pad cable to the console for providing a return path for the RF energy applied by the ablation handpiece. The ablation handpiece may additionally be coupled to the console via a handpiece cable. The ablation handpiece may be a disposable handpiece configured to deliver the RF energy used in the procedure and may also house a guidance sensor.

To provide the ultrasound image and guidance, the system may utilize either an ultrasound transducer which may be comprised of a rigid probe which connects to the console used in combination with a transducer sleeve which functions as a sleeve that houses the ultrasound transducer and a magnetic guidance sensor which connects to the console separate from the transducer. Alternatively, another embodiment of an ultrasound transducer with integrated magnetic guidance sensor may be used instead of the transducer and sleeve combination.

With respect to the electromagnetic field generator, either a Table Top Field Generator (TTFG) or a Planar Field Generator (PFG) may be used for connection to the console depending upon the type of hospital bed is available. The TTFG may generate a magnetic field that is picked up by the magnetic guidance sensors in the handpiece and the ultrasound transducer sleeve (or transducer with sensor) while the PFG may generate a magnetic field that is picked up by the magnetic guidance sensors in the handpiece and the ultrasound transducer sleeve (or transducer with sensor).

During use, when deploying the stylets from the ablation device, a deployment length of the stylets may be adjusted from any length of a partially extended configuration to a fully extended configuration. Depending upon the length of the deployed stylets from the ablation device, the size of the ablation zone surrounding the stylets will vary accordingly as well. Hence, the user may adjust the size of the ablation zone to match or correlate with the size of, e.g., a fibroid, as well as to minimize ablation of the tissue region surrounding the treated region.

To facilitate sizing of the treatment region, a visual representation of the ablation zone may be provided to the user so that the user may quickly confirm not only that the positioning of the ablation device relative to the treatment area is sufficient but also that the deployment length of the stylets is suitable for creating an ablation zone of sufficient size. Hence, a dynamic imaging system which automatically generates a visual representation of the ablation zone, based on specified parameters, may be provided.

One system for visualizing a tissue treatment may generally comprise a tissue treatment instrument having one or more deployable stylets and a first energy sensor and an ultrasound imaging instrument which may be configured to generate an ultrasound imaging plane and further having a second energy sensor. Additionally, an energy field generator may also be included which may be configured for placement in proximity to a patient body and which may be further configured to generate an output indicative of a position the first and second energy sensors relative to one another. Furthermore, the system may also include console in communication with the treatment instrument, ultrasound imaging instrument, and energy field generator, wherein the console is configured to generate a representative image of the tissue ablation instrument oriented relative to the ultrasound imaging plane and an ablation border or treatment zone based upon a deployment position of the one or more stylets.

One method of visualizing a tissue treatment may generally comprise receiving a first input from a tissue treatment instrument having one or more deployable stylets and a first energy sensor and receiving a second input from an ultrasound imaging instrument configured to generate an ultrasound imaging plane and further having a second energy sensor. A position and orientation of the tissue ablation instrument relative to the ultrasound imaging instrument may be displayed based upon an output received from an energy field generator placed in proximity to a patient body, wherein the output is indicative of a position and orientation of the first and second energy sensors relative to one another, and a representative image of an ablation border or treatment zone based upon a deployment position of the one or more stylets may also be displayed.

One system for tissue treatment may generally comprise a non-transitory computer readable medium for storing a computer readable program code, and a processor in communication with the non-transitory computer readable medium, the processor being configured to perform operations including: displaying an image of an ablation device having one or more deployable stylets, determining a size of an ablation border or cage based upon a deployment position of the one or more stylets, and displaying the ablation border or cage to a user.

One method of ablating may generally comprise displaying an image of an ablation device having one or more deployable stylets, tracking a deployment position of the one or more stylets when advanced from the ablation device, determining a size of an ablation border or cage based upon the deployment position of the one or more stylets, and displaying the ablation border or cage to a user.

The imaging and display systems described herein may be utilized in any combination with the devices and methods described in U.S. patent application Ser. No. 13/069,497 filed Mar. 23, 2011 (U.S. Pub. 2012/0245576), which is incorporated herein by reference in its entirety and for any purpose.

BRIEF DESCRIPTION OF THE DRAWINGS

A full understanding of the invention can be gained from the following description of the preferred embodiments when read in conjunction with the accompanying drawings in which:

FIG. 1A illustrates an ablation device useful with the inventive system.

FIGS. 9A to 9C illustrate graphic representations of the deployment of the stylets and the ablation zone being sized accordingly in the visual representation.

FIGS. 10A to 10C illustrate simultaneous images of the probe and the ultrasound image on a separate monitor or upon the same GUI as the ablation device.

FIGS. 11A to 11C illustrate one example of the deployed stylets having a selected deployed length and its corresponding ablation border or cage displayed upon the image.

FIGS. 12A to 12C illustrate simultaneous images of the intersection between the ultrasound image and ablation border or cage.

DETAILED DESCRIPTION OF THE INVENTION

Figure 1B:
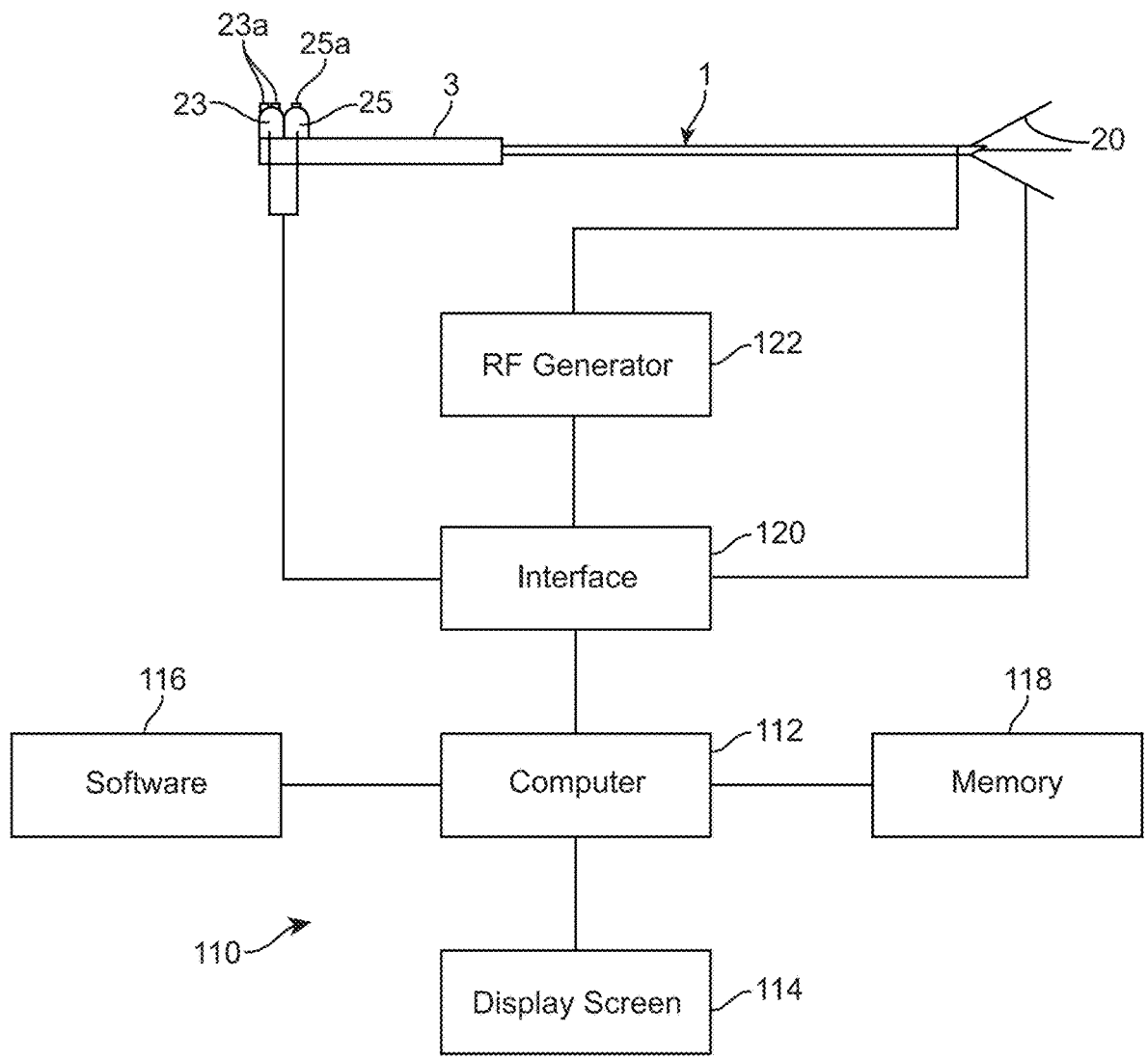
FIG. 1B illustrates an ablation system incorporating computer controls in accordance with the inventive system.

FIG. 1A is a perspective view of a multiple antennae or stylet ablation trocar instrument 1 useful in practicing the inventive system. Ablation instrument 1 comprises a cannula 2 which houses a plurality of stylets 20 and, optionally, a plurality of anchors 4. A trocar point 5 is provided at the distal end of cannula 2. At least one conductor 6 is provided within cannula 2. Conductor 6 is electrically coupled to stylets 20 and trocar point 4 and accordingly provides RF energy to stylets 20 and trocar point 5. In accordance with the invention, stylets 20 and trocar point 5 are electrically coupled to each other and electrically isolated from other exposed portions of ablation instrument 1. Stylets 20 and trocar point 5 are at the distal end of ablation instrument 1. Each of the stylets is made of thin wire-like tubular members and during the procedure is initially housed entirely within the cannula 2. In other variations, the stylets 20 and trocar point 5 may instead be configured to impart other forms of energy besides RF ablation energy. For example, the ablation instrument may instead be configured to deliver, e.g., cryo-ablation energy, plasma energy, mechanical energy (such as abrasion, cutting, etc.), or other forms of energy.

Stylets 20 are deployed for ablation by being advanced in the forward direction toward the distal end of ablation instrument 1 out from ablation instrument 1 through openings 7. As stylets 20 are advanced through openings 7, they bear against deflection surfaces 8. Deflection surfaces 8 are defined in the metal body which defines trocar point 5 at the distal end of the cannula 2.

During use of the inventive system, trocar point 5 at the distal end of cannula 2 is used to initially pierce the tissue of the fibroid tumor during use of the inventive ablation device 1. Optionally, a plurality of anchors 9, also housed within ablation instrument 1, may be deployed rearwardly toward the proximal end of ablation instrument 1. During deployment, anchors 9 are deflected by deflection surface 11 to move into the positions illustrated in FIG. 1. After deployment, anchors 9 may optionally be used to prevent rearward movement of trocar point 5 during deployment of stylets 20.

Stylets 20 are deployed through the use of a slideably mounted operator member 13 housed within cannula 2 and coupled to an operating handle at its proximal end. Anchors 9 are also deployed through the use of a slideably mounted operator member (not illustrated) housed within cannula 2 and coupled to an operating handle at its proximal end. The distal end of operator member 13 is coupled to stylets 3 which may thus be advanced an identical distance in unison. The retraction and deployment of anchors and stylets is controlled by an operator handle 3 as illustrated in FIG. 1B.

Figure 1C:
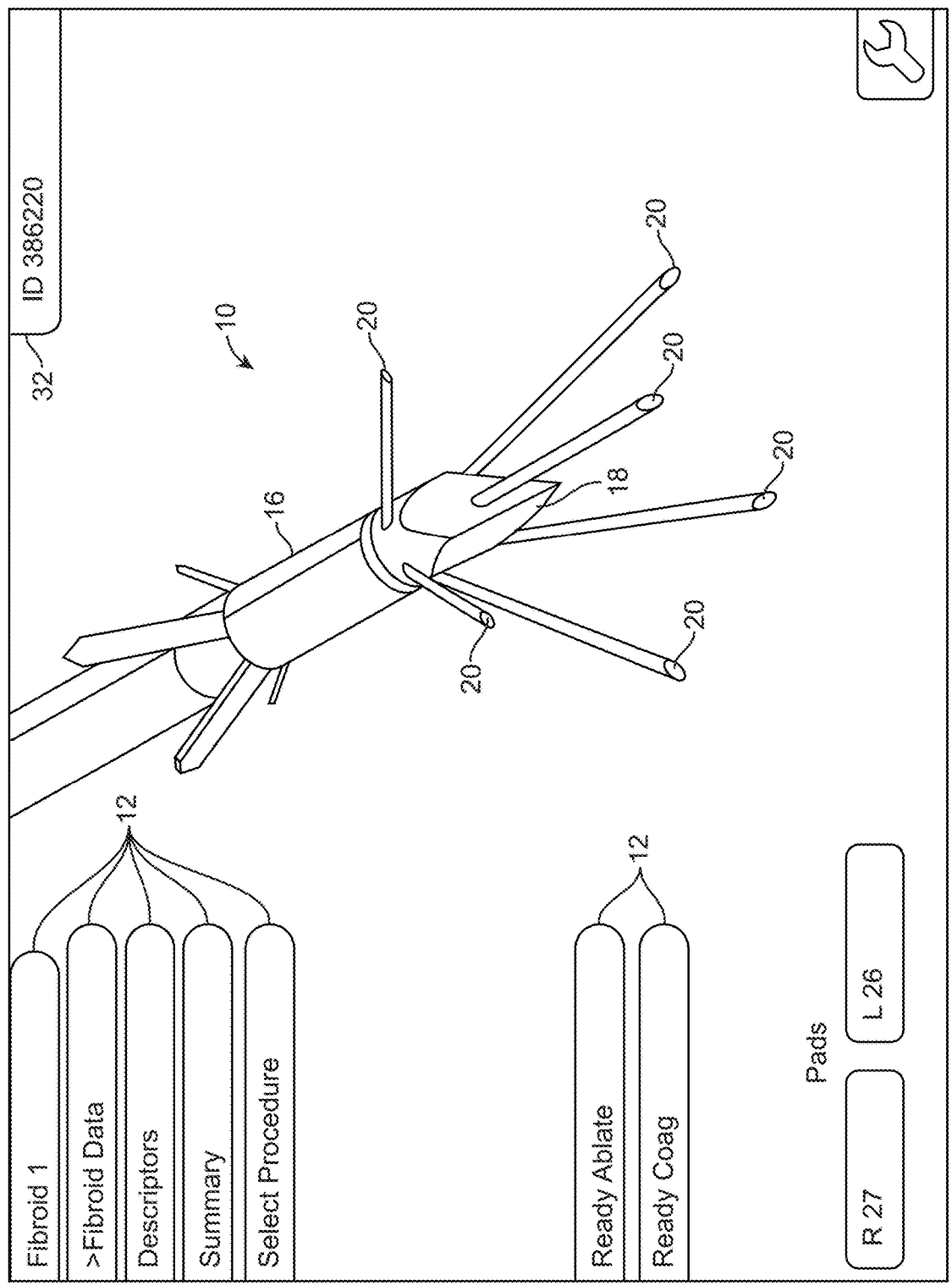
FIG. 1C shows the graphical user interface screen in which menus "fibroid data", "descriptor", "summary", "select procedure", "ready ablate" and "ready coag" are displayed, and the navigational tool has scrolled to the menu choice "fibroid data".

Referring to FIG. 1C, a graphical user interface (GUI) 10 display screen is shown. A surgeon uses a medical device such as an ablation device. The ablation device is illustrated in GUI 10 by ablation device illustration 16. The ablation device is used for ablating tissue masses. Use of the same is facilitated by GUI 10 and the navigational button matrix to minimize the likelihood of breaking the sterility of the surgical field. The GUI 10 displays a choice of menu items 12 that the practitioner can scroll through by depressing the scroll button 23 (FIG. 1B) which carries two raised dots 23a on its surface on the navigational button matrix. All of the menu items 12 are displayed at the same time. The menu items 12 allow the surgeon or other practitioner to enter patient data, collect patient data and perform a surgical procedure all within the sterile field. When a desired menu is reached, the surgeon selects from menu items 12 by depressing the select button 25, which has one raised dot 25a on its top surface, on the navigational button matrix, which may be viewed as a whole as a navigational tool. When ablating a tissue mass such as a fibroid tumor, the menu 12 choices comprise the "Fibroid" number data, "Fibroid Data", "Descriptors", "Summary", "Select Procedure", "Ready Ablate" and "Ready Coag". In FIG. 1B, the system indicates that information with respect to a first fibroid, "Fibroid 1", is being collected. An arrow indicator indicates that the surgeon has scrolled to the "Fibroid Data" menu item. Repeated depression of the scroll button causes the arrow indicator to move in sequence through the choices comprising menu items labeled "Fibroid" for the fibroid number, "Fibroid Data", "Descriptors", "Summary", "Select Procedure", "Ready Ablate" and "Ready Coag". Stopping on the fibroid number data which is labeled "Fibroid 1" in FIG. 1B (which results in placing the arrow indicator before the indication "Fibroid 1"), and depressing of the select button results in causing the arrow indicator to cursor through indicators reading "Fibroid 1", "Fibroid 2", "Fibroid 3", "Fibroid 4", "Fibroid 5" and so forth. If one next depresses the scroll button, arrow indicator 15 indicates selection of "Fibroid Data". As an alternative, one also can scroll to the "Fibroid Data", push select, scroll to the numbers until the desired fibroid number is presented (for example "Fibroid 2"), and click the select button resulting in the display of "Fibroid 2" instead of "Fibroid 1".

An exemplary system for implementing the above invention is illustrated in FIG. 1B. Generally, the system 110 comprises a computer 112. Computer 112 may be any control device, such as a microprocessor, personal computer or a more powerful or less powerful computer with a typical personal computer-type operating system. Computer 112 includes a display screen 114, which may optionally be a touchscreen to provide a second means of navigation.

Personal computer 112 also incorporates software 116. Software 116 may be of any type for use on any suitable computing device, and which may be easily written by a programmer of ordinary skill in the art who is informed by this specification. The software is responsive to produce images illustrated in the drawings and stored in a memory 118 of computer 112. The software performs the navigation functions described above, being responsive to touchscreen entry and/or scroll and select buttons 23 and 25 on ablation instrument 1.

Computer 112 communicates with ablation instrument 1 through an interface board 120 which is coupled to scroll and select buttons 23 and 25. Likewise, in response to operation by touching on display screen 114 or operation of scroll and select buttons 23 and 25, computer 112 may cause RF generator 122 to apply power to the trocar point for ablation. In response thereto, thermocouples on stylets 20 will generate temperature indicating signals which are coupled through suitable interface electronics to computer 112, allowing the computer to control application of RF generator by RF generator 122, to display temperature information, operate alarms, to terminate the application of RF energy, and to perform any other design controls in response thereto, for example as described above.

In accordance with U.S. Pat. No. 6,840,935 issued to Lee on Jan. 11, 2005 and which is incorporated herein in its entirety and for any purpose, uterine ablation may be implemented with imaging provided through the use of a laparoscope imaging arrangement and an ultrasound imaging device. The images generated by the laparoscope and the ultrasound device are provided on separate monitors. Other examples of devices which may be utilized with the features described herein are disclosed in further detail in U.S. Pat. Nos. 7,678,106; 8,080,009; 8,512,333; 8,512,330; 9,662,166; 9,861,426; 9,510,898; 8,241,276; and 8,251,991. Each of these references is incorporated herein by reference in its entirety and for any purpose.

It is contemplated that the display may include touch-screen controls and/or menu options for controlling other devices. For example, the display may provide for navigation to a control menu for controlling display characteristics for the ultrasound viewing device, a control menu for selecting metering functions for inclusion on the display, such as heartbeat, or for selection between ultrasound and laparoscopic images.

The system may also incorporate means for varying the various menu functions described above incorporated into the software which controls the system. Such means may comprise accessing menu choices and display options using a keyboard.

The display of menu options (and the other GUI elements, or some of them) may also be incorporated into the display of, for example, the ultrasound image used by the physician. Other types of images may also be employed. More particularly, with reference to FIG. 2, the inventive system 210 utilizes an ablation probe 212. Ablation probe 212 includes a multi-button keypad 214, for example with scroll and select switches.

In the manner of the earlier embodiment, temperature signals and keypad control information is coupled to a computer interface 216 which sends this information to personal computer 218. Personal computer 218 drives a computer display 220 which includes a navigation menu 222 of the type described above.

Personal computer 218 through interface board 224 controls ablation energy source 226. At the same time, an ultrasound probe 228 coupled to an ultrasound machine 230 provides ultrasound image information to interface 224 which in turn provides this information to personal computer 218 for display on computer display 220.

Figure 2:
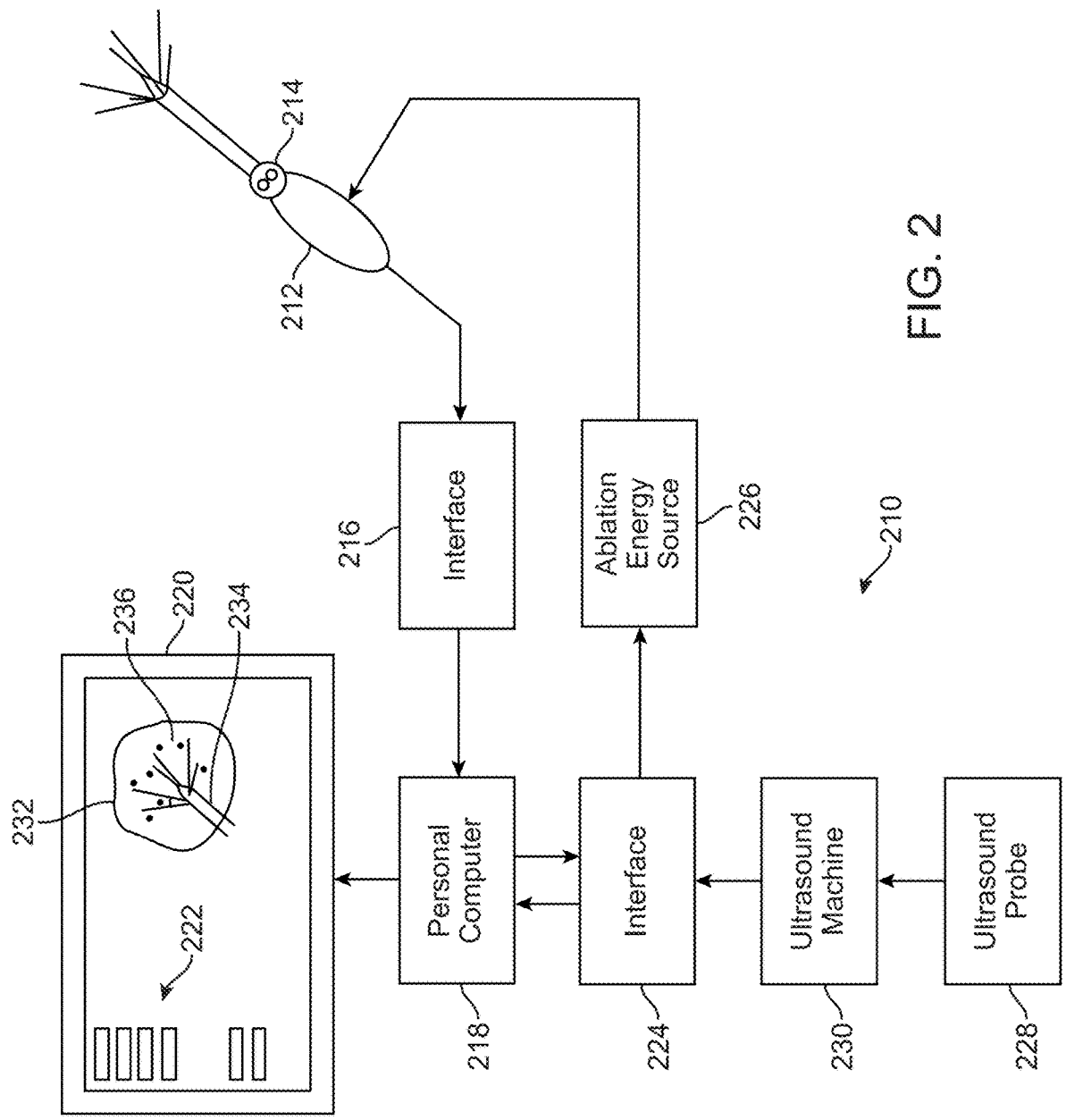
FIG. 2 illustrates an alternative inventive system where imaging data is displayed on the GUI.

Using the system of FIG. 2, the surgeon may concentrate on a single monitor displaying both ultrasound, and device performance information and a means for control of the system. More particularly, computer display 220 displays, for example, the fibroid 232 being operated on, an image 234 of probe 214 and an image 236 of temperature data. The positioning of the images 234 and 236 may be done by the computer using a pattern matching or other strategy.

Figure 3:
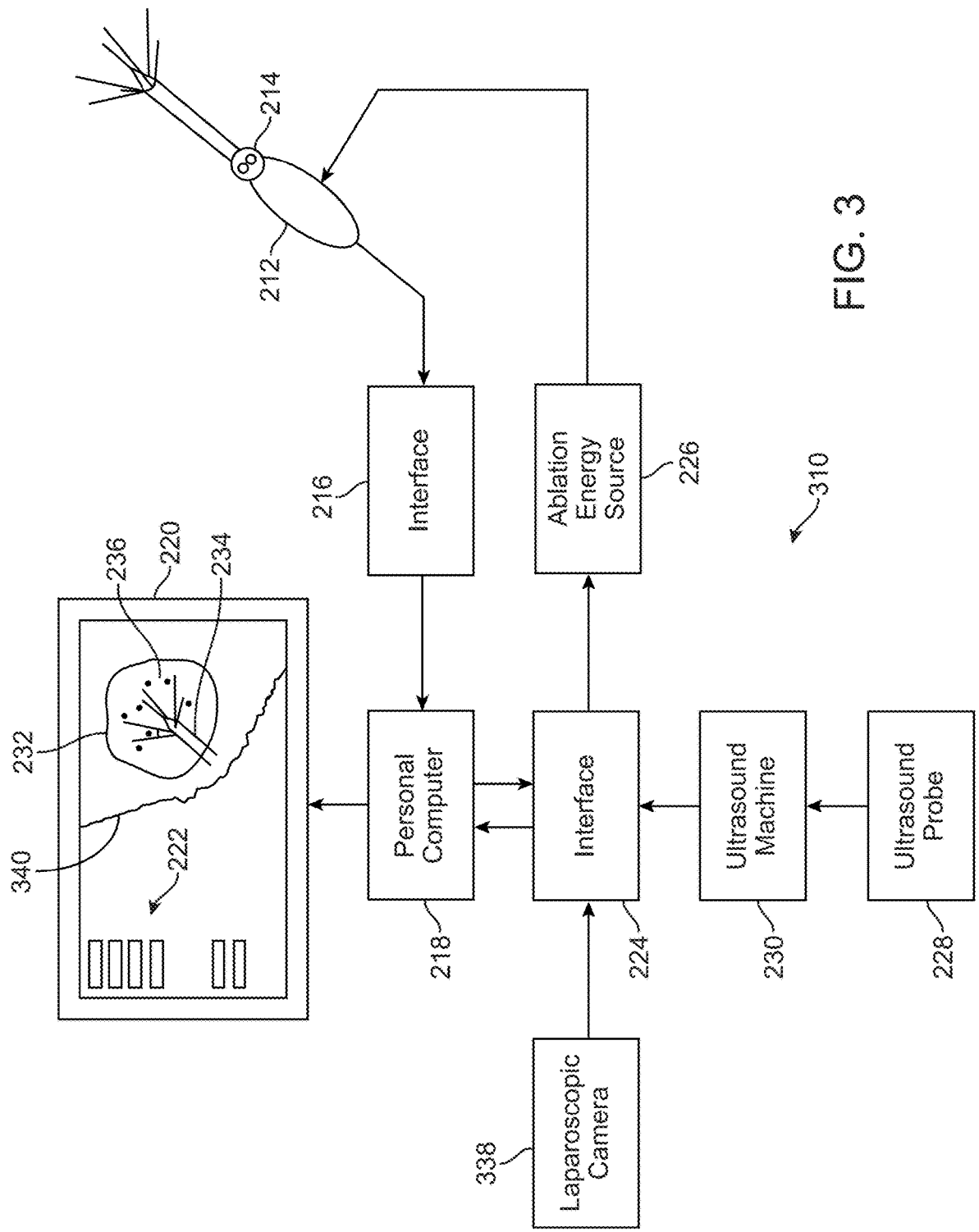
FIG. 3 illustrates an alternative inventive system where imaging data from two different image sources is merged and displayed on the GUI.

Another embodiment is illustrated in FIG. 3. The operation of the system 310 of FIG. 3 is substantially the same as that of the system in FIG. 2, except for the addition and integration of an image from a laparoscope.

More particularly, a laparoscopic camera 338 is coupled to interface 224. Camera 338 produces an image of the outside of the uterus resulting in display of an image 340 of the uterus on computer display 220 superimposed over the image 232 of the fibroid obtained using ultrasound. It is noted that images 232 and 340 are positioned in the same manner as the fibroid and the uterus are positioned in the patient, thus giving a more complete picture of the state of the surgery.

Accordingly, the system may be composed of different components into a comprehensive overall system which may integrate an RF ablation component 226, an ultrasound system 230, and a guidance mapping system. The combination of these components may allow for the user to seamlessly integrate ultrasound and guidance to help position the ablation probe 212 relative to the tissue for treatment. The combination of the various individual components into a seamless system enables for the continuous monitoring, feedback, and accuracy of treatment as the ultrasound probe 228 may communicate and obtain instant feedback to better manage the treatment outcomes. For example, having the ultrasound probe 228 work in conjunction with the guidance system enables the guidance to integrate, interpret, and respond to the ultrasound images in real time.

Accordingly, a single console may be used to integrate each of the different components and computer into an overall coherent system which facilitates the communication between each of the sub-systems. Hence, the RF ablation component 226 may have the ablation probe 212 interact with an electromagnetic field generated by the guidance mapping system to generate ablation probe positional information for spatial tracking. The computer 218 may be responsive to the ultrasound probe 228 positional information and the ablation probe 212 may generate a graphic representation showing the positional relationship between the ultrasound image and the ablation probe 212 to guide placement of the ablation probe 212 into an anatomical location imaged by the ultrasound probe 228. Hence, in one embodiment, the computer 218 and interface 224 as well as interface 216 and ablation energy source 226 and ultrasound machine 230 may all be integrated into a single console, as described in further detail herein.

The apparatus additionally comprises a display device responsive to the computing device so as to display a graphic representation. The display may comprise a guidance animation displayed on the GUI, which is generated by the computing device 218, which processes the guidance information. Real-time correctional information can be viewed by a user in the guidance animation.

The guidance system may use the electromagnetic spatial tracking to calculate the position and orientation of sensors within a defined volume. The sensors may accordingly be embedded in the tip of the ablation probe 212 and ultrasound probe 228 or within or along an ultrasound transducer sleeve having the sensors, as described in further detail herein. The computer 218 may determine the position and orientation relative to one another within the patient's abdominal cavity and display representative animated images on a GUI. The acquired ultrasound images may be displayed in a seamless integrated image with the representative animated images.

The guidance system is disclosed in further detail in U.S. patent application Ser. No. 14/872,507 filed Oct. 1, 2015 (U.S. Pub. 2016/0095537), which is incorporated herein by reference in its entirety and for any purposes.

Figure 4A:
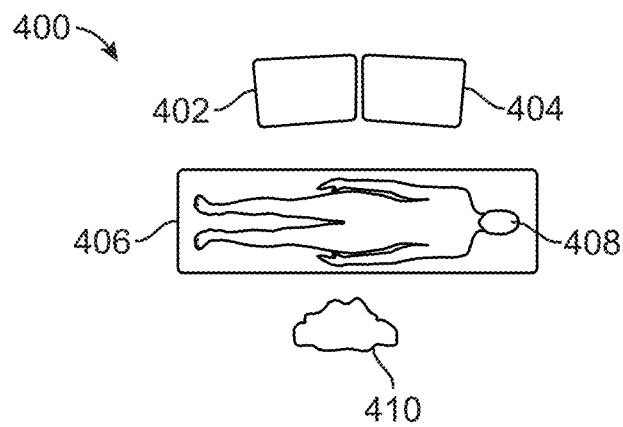
FIGS. 4A to 4D illustrate representative examples for various configurations in positioning display monitors relative to the patient.

Given the integration of multiple images and instruments, there may be several configurations for positioning of the display monitors relative to the patient and the practitioner to facilitate a treatment procedure. For instance, FIGS. 4A to 4D show representative examples for various configurations. FIG. 4A shows one example in which the monitors 400 may be positioned at the right side of the patient 408 who is laying supine upon the surgical table 406. The practitioner 410 may be positioned directly across from the monitors 400 at the left side of the patient 406. The monitors 400 may be positioned such that a first monitor 402 showing images for guidance is positioned to the left and a second monitor 404 showing ultrasound images is positioned to the right relative to the practitioner 410.

Figure 4B:
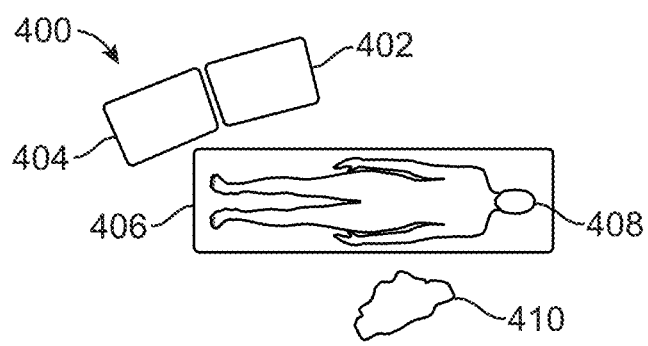
Figure 4C:
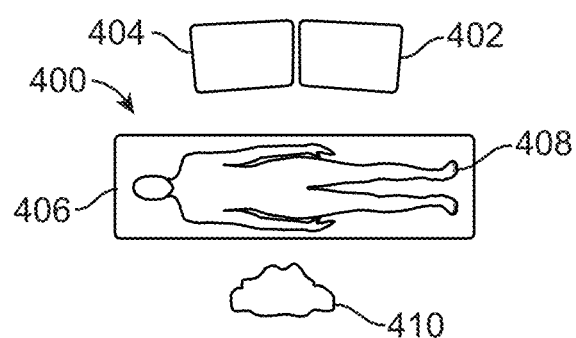
Figure 4D:
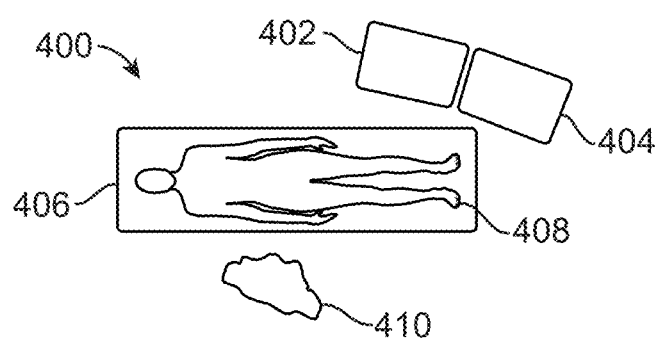

FIG. 4B shows another variation in which the monitors 400 may be positioned at the feet of the patient across from the practitioner 410. The first monitor 402 showing images for guidance may be positioned to the right and the second monitor 404 showing the ultrasound images may be positioned to the left relative to the practitioner 410. FIG. 4C shows yet another variation in which the monitors 400 are positioned to the left side of the patient 408 and the practitioner 410 is positioned to the right side of the patient 408. The first monitor 402 may be positioned to the right while the second monitor may be positioned to the left relative to the practitioner 410. In yet another variation, FIG. 4D shows a configuration in which the monitors 400 are positioned at the feet of the patient 408 to their left but the first monitor 402 is positioned to the left and the second monitor 404 is positioned to the right relative to the practitioner 410.

While the second monitor 404 showing the ultrasound images may generally be positioned closest to a monitor showing images from the laparoscopic camera 338, these configurations are intended to be illustrative of different embodiments and are not intended to be limiting as other configurations may be possible.

Figure 5:
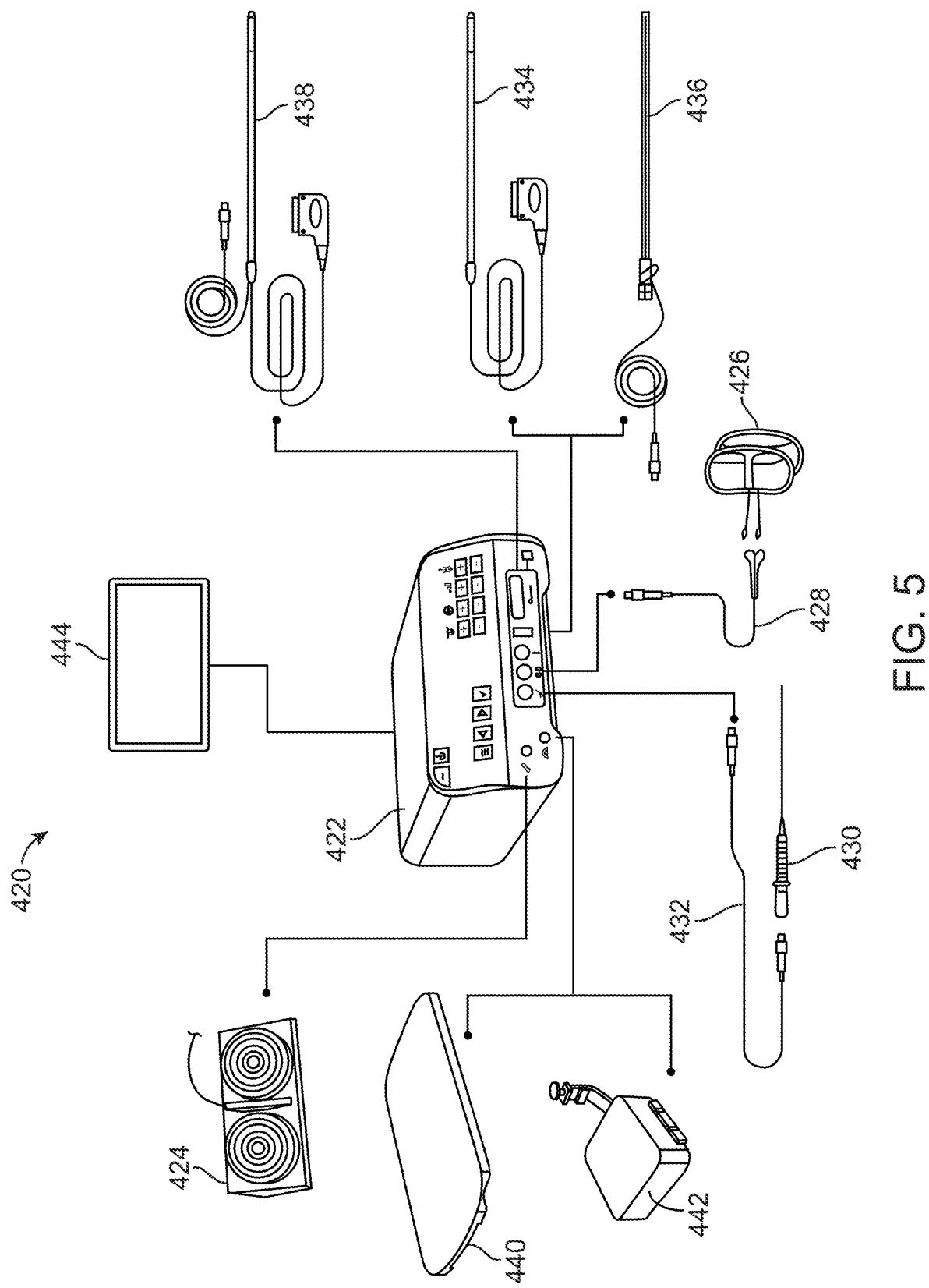
FIG. 5 illustrates an illustrative perspective view of one variation of the console configured to receive the connections or signals from each of the various components for integrating them into a seamless user interface.

Turning now to the console 422 which may integrate each of the different components, FIG. 5 shows an illustrative perspective view of one variation of the console 422 configured to receive the connections or signals from each of the various components for integrating them into a seamless user interface. The console 422 may be coupled to a monitor 444 such as a hospital-owned accessory monitor for displaying the generated information via, e.g., a HDMI to DVI cable. A foot pedal 424 (e.g., pneumatic dual-foot pedal) may be coupled to the console 424 and used to selectively active the ablation probe so that RF energy may be turned ON and OFF.

One or more pads 426 (e.g., disposable set of 2 units) may also be coupled via a pad cable 428 to the console 422 for providing a return path for the RF energy applied by the ablation handpiece. The ablation handpiece 430 may additionally be coupled to the console 422 via a handpiece cable 432 as shown. The ablation handpiece 430 may be a disposable handpiece configured to deliver the RF energy used in the procedure and may also house a guidance sensor. The ablation handpiece 430 is described in further detail in herein.

To provide the ultrasound image and guidance, the system may utilize either an ultrasound transducer 434 which may be comprised of a rigid probe which connects to the console 422 used in combination with a transducer sleeve 436 which functions as a sleeve that houses the ultrasound transducer 434 and a magnetic guidance sensor which connects to the console 436 separate from the transducer 434. Alternatively, another embodiment of an ultrasound transducer 438 with integrated magnetic guidance sensor may be used instead of the transducer 434 and sleeve 436 combination.

With respect to the electromagnetic field generator, either a Table Top Field Generator (TTFG) 440 or a Planar Field Generator (PFG) 442 may be used for connection to the console 422 depending upon the type of hospital bed is available. The TTFG 440 may generate a magnetic field that is picked up by the magnetic guidance sensors in the handpiece 430 and the ultrasound transducer sleeve 436 (or transducer with sensor 438) while the PFG 442 may generate a magnetic field that is picked up by the magnetic guidance sensors in the handpiece 430 and the ultrasound transducer sleeve 436 (or transducer with sensor 438). The PFG 442 may include an optional mounting arm to connect the PFG 442 to the hospital bed or platform that the patient may lie down upon. In other embodiments, the electromagnetic field generator may instead be configured to generate other forms of energy, e.g., RF energy, microwave energy, ultrasound energy, infrared energy, or other forms of energy which may enable the device to produce a sensing field or array for detecting the guidance sensors (which may be suitably configured depending on the form of energy) in the handpiece 430 and ultrasound transducer sleeve 436 (or transducer with sensor 438).

Figure 6:
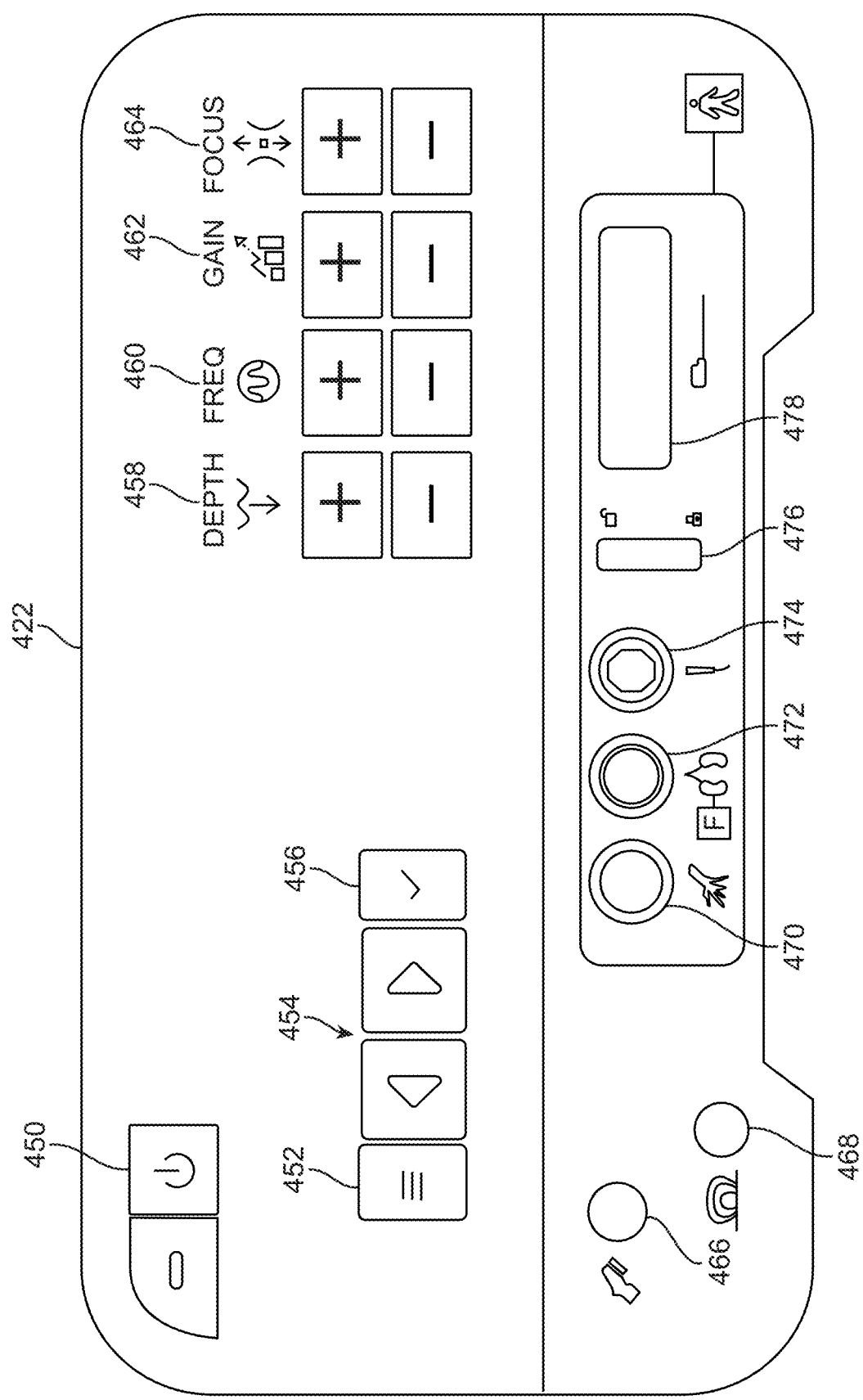
FIG. 6 illustrates one variation of the console showing the various controls and interface connections.

The console 422 may include a number of actuation and alert or indicator features for each of the various components connected. As shown in the front view of FIG. 6 of one variation of console 422, the console 422 may include an on/standby button 450 optionally having an indicator such as an LED indicator for turning the console 422 ON and OFF. For instance, pushing the button 450 may turn the console 422 ON (e.g., LED will turn green) and an additional push will shut the console 422 OFF. If emergency RF shutoff is needed during ablation, the user can turn off the RF power by momentarily pressing the button 450 again. A menu button 452 may be actuated to bring up a menu to access the user-adjustable settings where menu scroll buttons 454 may be actuated to allow the user to scroll through the menu items (e.g., full-screen ultrasound mode, ablation volume guide on/off, coagulation power level, OR setup menu, and sound volume, etc.) and a check button 456 may be actuated to accept a selected menu item.

An ultrasound depth adjustment button 458 may be actuated to adjust the depth or magnification of the ultrasound image (e.g., supported ultrasound depths are: 3 cm, 4 cm, 5 cm, 6 cm, 7 cm, 8 cm, 9 cm, etc.) and an ultrasound frequency adjustment button 460 may be actuated to adjust the frequency of the ultrasound (e.g., supported frequencies are: 5 MHz, 6 MHz, 9 MHz, 12 MHz, etc.) and an ultrasound gain adjustment button 462 may be actuated to adjust the gain of the ultrasound. An ultrasound focus adjustment button 464 may be actuated to move the focus of the ultrasound (e.g., supported focal depths are: 0.2 cm, 0.4 cm, 0.7 cm, 1 cm, 1.4 cm, 1.8 cm, 2.3 cm, 3 cm, 4 cm, 5 cm, 6 cm, 8 cm, etc.).

The dual-foot pedal connector 466 is shown for accepting the connector from the foot pedal 424 and the field generator connector 468 is also shown for accepting the connector from either the TTFG 440 or PFG 442. The handpiece connector 470 is shown for accepting either end of the handpiece cable 432 and the return pad connector 472 is shown for accepting the connector from the pad cable 428. The transducer sensor connector 474 is shown for accepting the cable from either the transducer sleeve 436 or from the sensor cable from the transducer with sensor 438. A transducer connector lock 476 may be actuated to lock the transducer connector in place and the transducer connector 478 may receipt the connector from the transducer 434 or 438.

The variation of the console 422 is shown for illustrative purposes and other configurations are intended to be within the scope of this description.

Figure 7A:
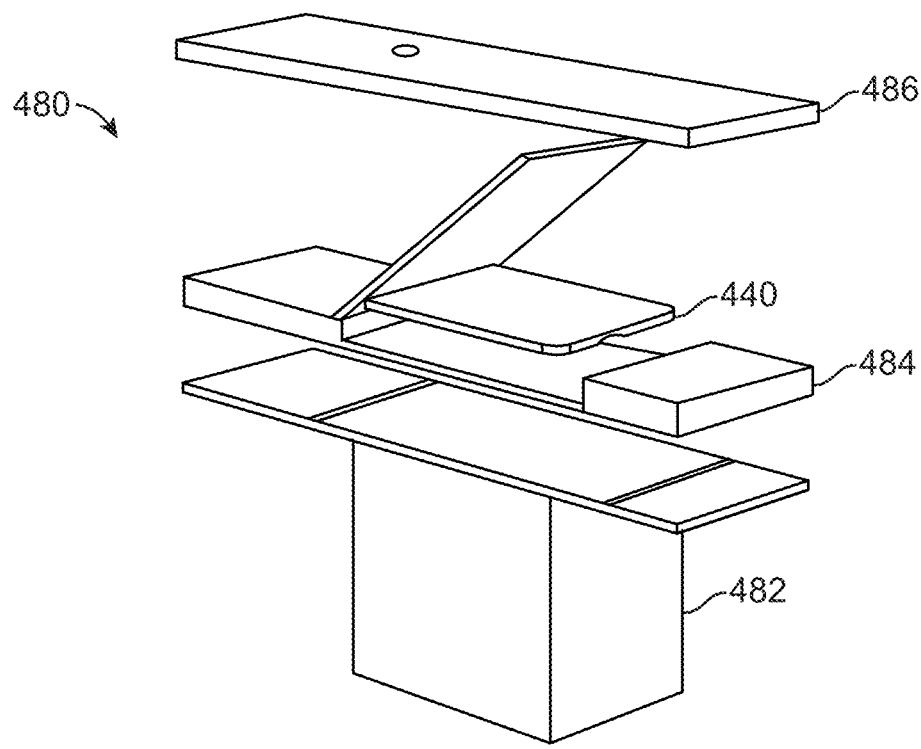
FIGS. 7A and 7B illustrate perspective views of different variations for positioning of an electromagnetic field generator relative to an operating room table.
Figure 7B:
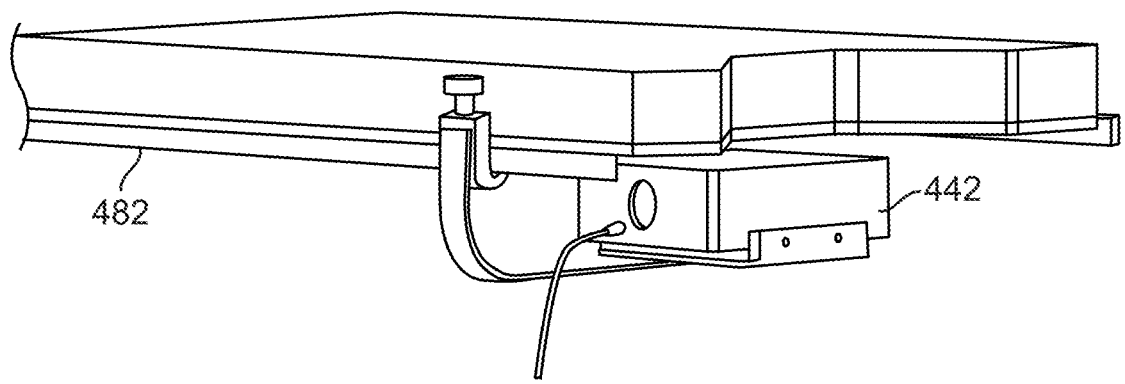

As described herein and as further described in U.S. patent application Ser. No. 14/872,507 filed Oct. 1, 2015 (U.S. Pub. 2016/0095537), which has been incorporated herein by reference, the platform upon which the patient lies upon may incorporate an electromagnetic field generator in communication with the computer within the console 422 for obtaining navigational imaging data to obtain relative orientation information of the handpiece 430 and/or ultrasound transducer 436 or 438. If the operating room table 482 is fabricated from steel, a TTFG pad set 484 configured to receive a TTFG unit 440 may be placed upon the table 482 and the TTFG 440 may be positioned upon the pad set 484 such that the patient's pelvis is centered directly above the TTFG 440. A standard operating room table pad set 486 may then be placed over the pad set 484 and TTFG 440, as shown in the perspective view of FIG. 7A. In the event that the operating room table is fabricated from a radiolucent or fiberglass material, the PFG 442 unit may be mounted below the table 482, as shown in the perspective view of FIG. 7B, e.g., upon a bed rail, opposite to the practitioner.

The patient may lay on top of TTFG 440 or PFG 442 which has been located in a plane substantially parallel to the plane of the operating table 482. The option of placing the patient in the supine position over a flat horizontal electromagnetic field generator resting on the operating table, in many circumstances, presents advantages, including allowing for more accurate and convenient imaging, the absence of an obstruction in the operating area, eliminating the need for wider operating tables, and simplifying and minimizing the physical structures in the operating area, thus improving likelihood of maintaining a sterile field. At the same time, the system provides the additional value of protecting the horizontal electromagnetic field generator from damage.

The TTFG 440 or PFG 442 creates an electromagnetic field that extends through, for example, the torso of the human body that has been positioned over the electromagnetic field generator. The ultrasound probe 434, 436 or 438 interacts with the generated electromagnetic field to generate ultrasound probe positional information. The ultrasound probe 434, 436 or 438 is adapted to generate an ultrasound image of a region having a known spatial relationship to the probe. The console 422 is responsive to the ultrasound probe positional information and the ablation probe handpiece 430 generates positional information which appears as a graphic representation showing the positional relationship between the ultrasound image and the ablation probe to guide placement of the ablation probe handpiece 430 into an anatomical location imaged by the ultrasound probe 434, 436 or 438. The system additionally comprises a display device responsive to the computing device so as to display a graphic representation. The display may comprise a guidance animation displayed on the display device, which is generated by the computing device, which processes the guidance information. Real-time correctional information can be viewed by a user in the guidance animation.

After using standard ultrasound imaging to locate and map, e.g., a fibroid for treatment, the guidance system can be used to help determine the optimum location to enter the uterus with the tip of the ablation device 16. The guidance system feature can be used as an adjunct to the standard ultrasound image to assist the positioning of the ablation device 16 during a procedure and shows where the tip of the ablation device 16 would intersect the ultrasound plane 352. Once the tip of the ablation device 16 penetrates the uterine serosa, ultrasound visualization may be used to complete the process of positioning the ablation device 16 in the fibroid for treatment.

Examples of the how positional and orientation information from the ablation probe handpiece 430 and ultrasound probe 434, 436 or 438 may be combined by the console 422 into a comprehensive GUI are shown in FIGS. 8A to 8D. The integrated images are illustrated in the interface 490 which shows a first GUI 350 illustrating a three-dimensional (3D) view of the representative ultrasound transducer 228 and ultrasound plane 352 and a relative position of the representative ablation device 16. A second GUI 350' may show a two-dimensional representation (e.g., avatar) of the ultrasound transducer 228 and the ablation device 16 in real time as they are being positioned within the abdominal cavity. It places the image from the ultrasound machine onto a virtual ultrasound transducer plane 352 and displays a "Target Zone" with, e.g., purple lines, as an indicator of where the ablation device 16 shaft will intersect the ultrasound transducer plane 352.

Figure 8A:
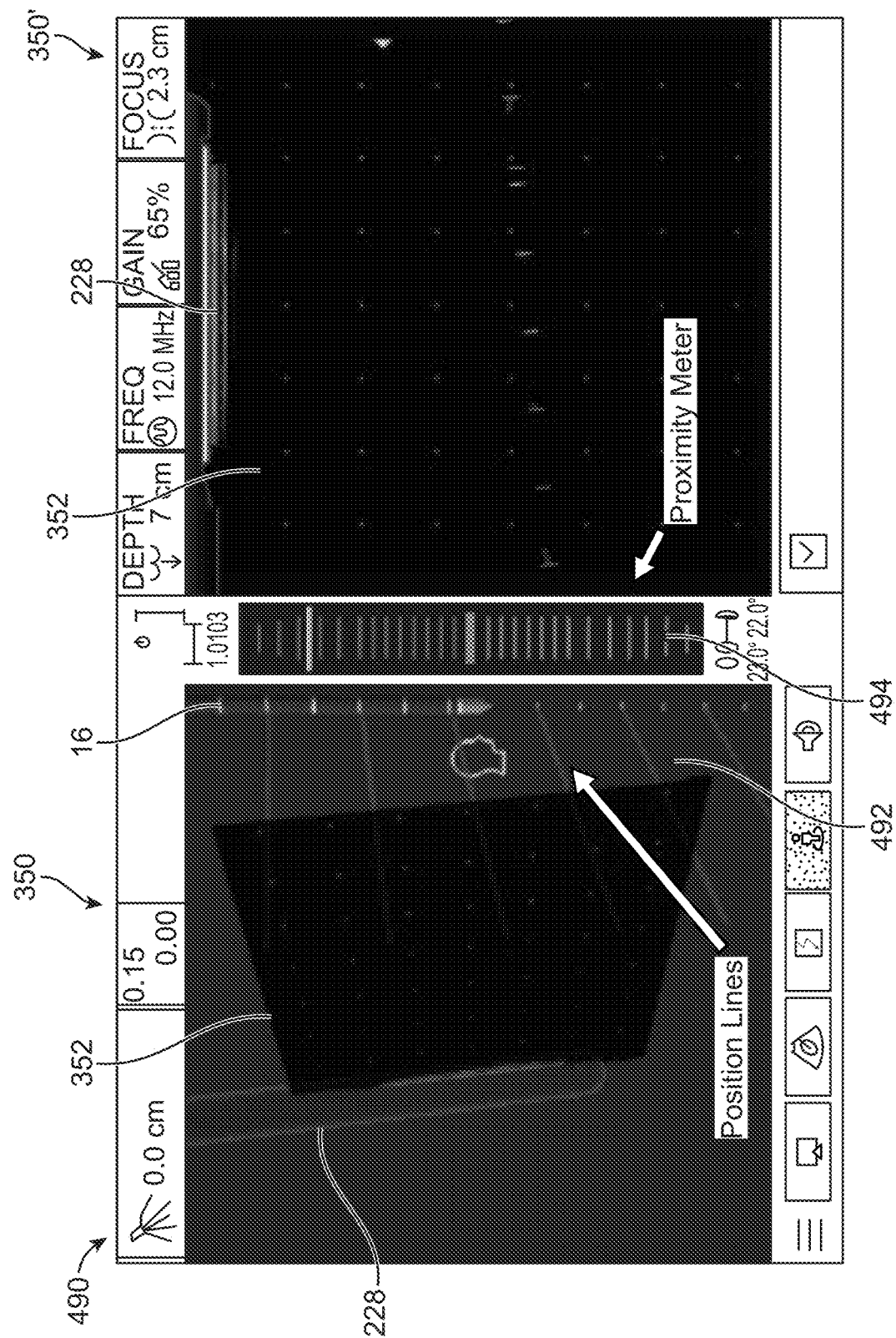
FIGS. 8A to 8D illustrate how positional and orientation information from the ablation probe handpiece and ultrasound probe may be combined by the console into a comprehensive user interface.

As shown in FIG. 8A, position lines 492 may be displayed upon the 3D GUI 350 and provided as an indication of an expected trajectory of the representative ablation device 16 relative to the transducer plane 352. If the trajectory is "in front" of the ultrasound plane 352, this portion of the trajectory may be shown as a first color, e.g., as yellow lines, whereas the portion of the trajectory situated "behind" the ultrasound plane 352 may be represented in a second color, e.g., as blue lines. A proximity meter 494 may also be included in the interface 490 located, e.g., between the GUI 350 and 350' where the proximity meter 494 may show a position of the ablation device 16 tip relative to the ultrasound plane 352. This may be helpful when approaching the targeted tissue region with the tip of the ablation device 16 within the plane 352 of the ultrasound. If the tip is shown "in front of" the plane 352, the bars may be displayed upon the proximity meter 494 in a first color, e.g., yellow, but if the tip of the ablation device 16 is "behind" the plane 352, the bars may be displayed in a second color, e.g., blue. When the tip of the ablation device 16 is positioned "on plane" with the ultrasound image 352, the bars of the proximity meter may be shown in a third color, e.g., green.

Figure 8B:
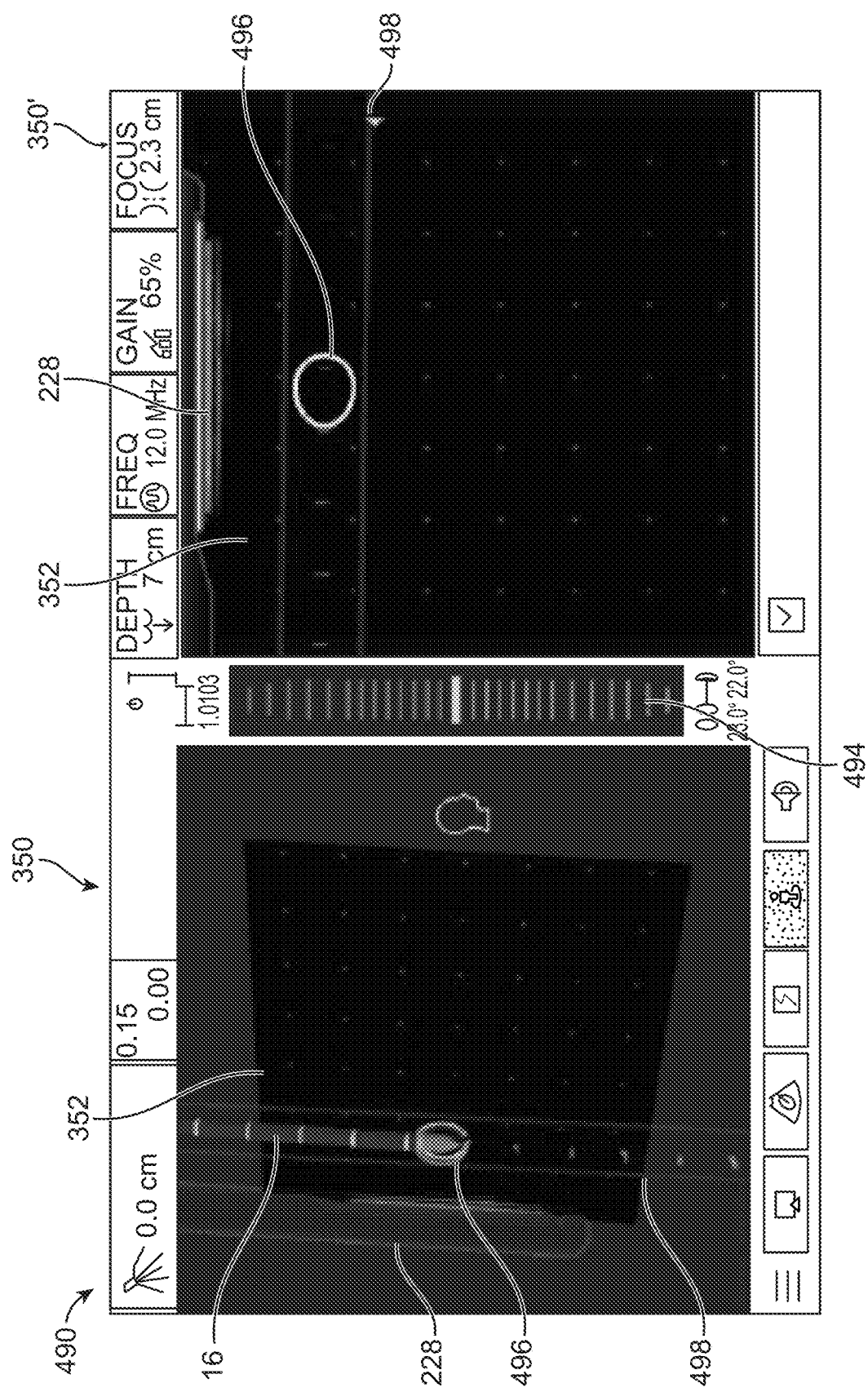
Figure 8C:
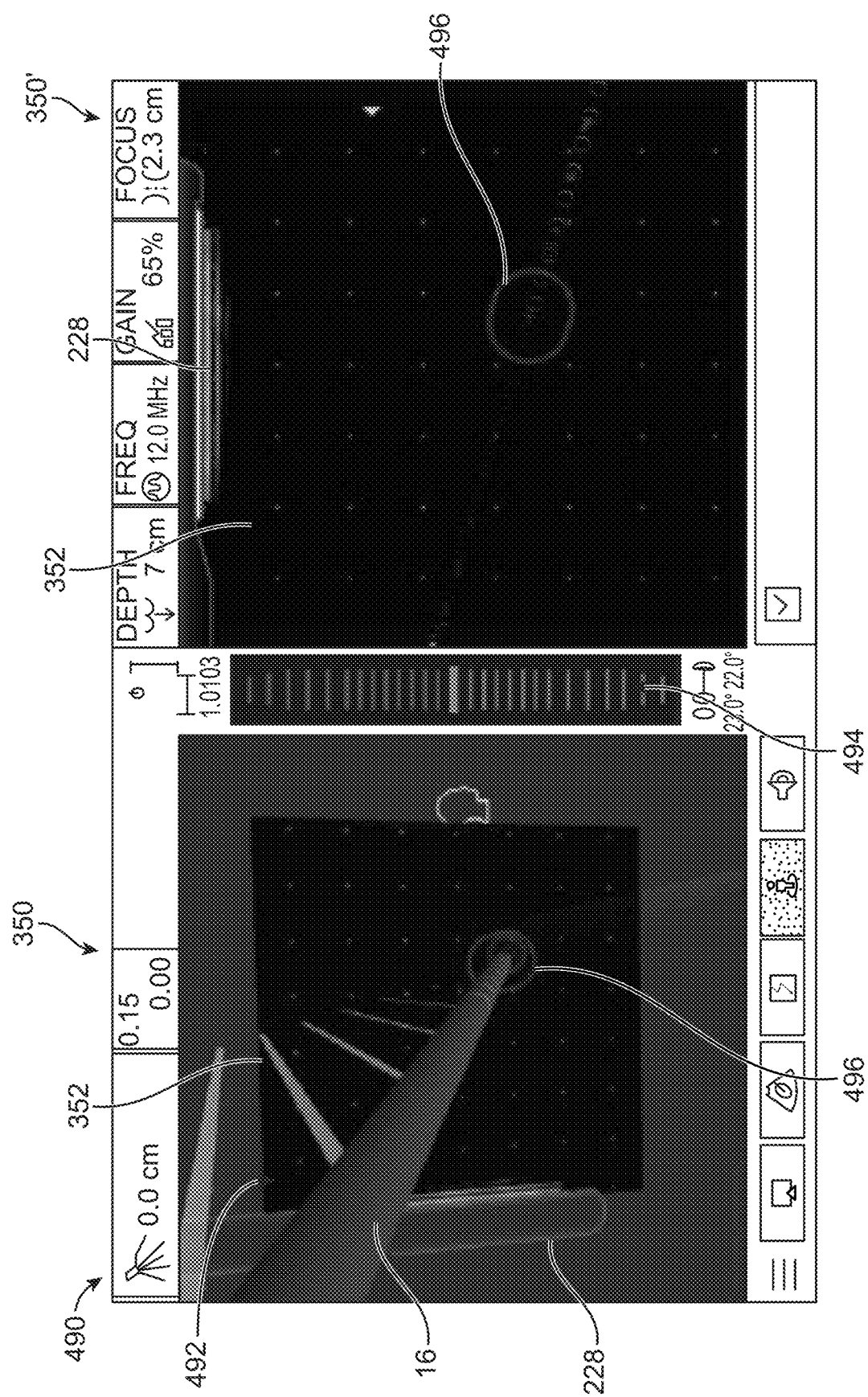

FIGS. 8B and 8C show another example in interface 490 in which the GUI 350, 350' may include an ablation handpiece-ultrasound "Target Zone" in which the software may provide a prediction of the path and projected intersection point of the ablation device 16 with the ultrasound plane 352 (target zone 496), so the user can orient the ablation device 16 relative to the target fibroid before insertion. The target zone 496 may be shown in both the GUI 350, 350' views as an obround-shaped indicator which is superimposed over the ultrasound scan plane 352. The size of the obround (a shape made of two semicircles connected by parallel lines tangent to their endpoints) may changes with the angle of the ablation device 16 relative to the ultrasound scan plane 352 so that when the ablation device 16 is perpendicular to the scan plane 352, the target zone 496 obround is a circle, and as the angle decreases toward parallel, the target zone 496 obround is shown as two lines capped with semi-circles at the ends. The ablation device 16 trajectory hash marks 498 may be displayed in both the GUI 350, 350' views. The hash marks 498 may be displayed as, e.g., red and yellow marks, when the ablation device 16 trajectory is distal to the ultrasound scan plane 352 and as, e.g., green hash marks, when the ablation device 16 trajectory is within the ultrasound plane 352.

Figure 8D:
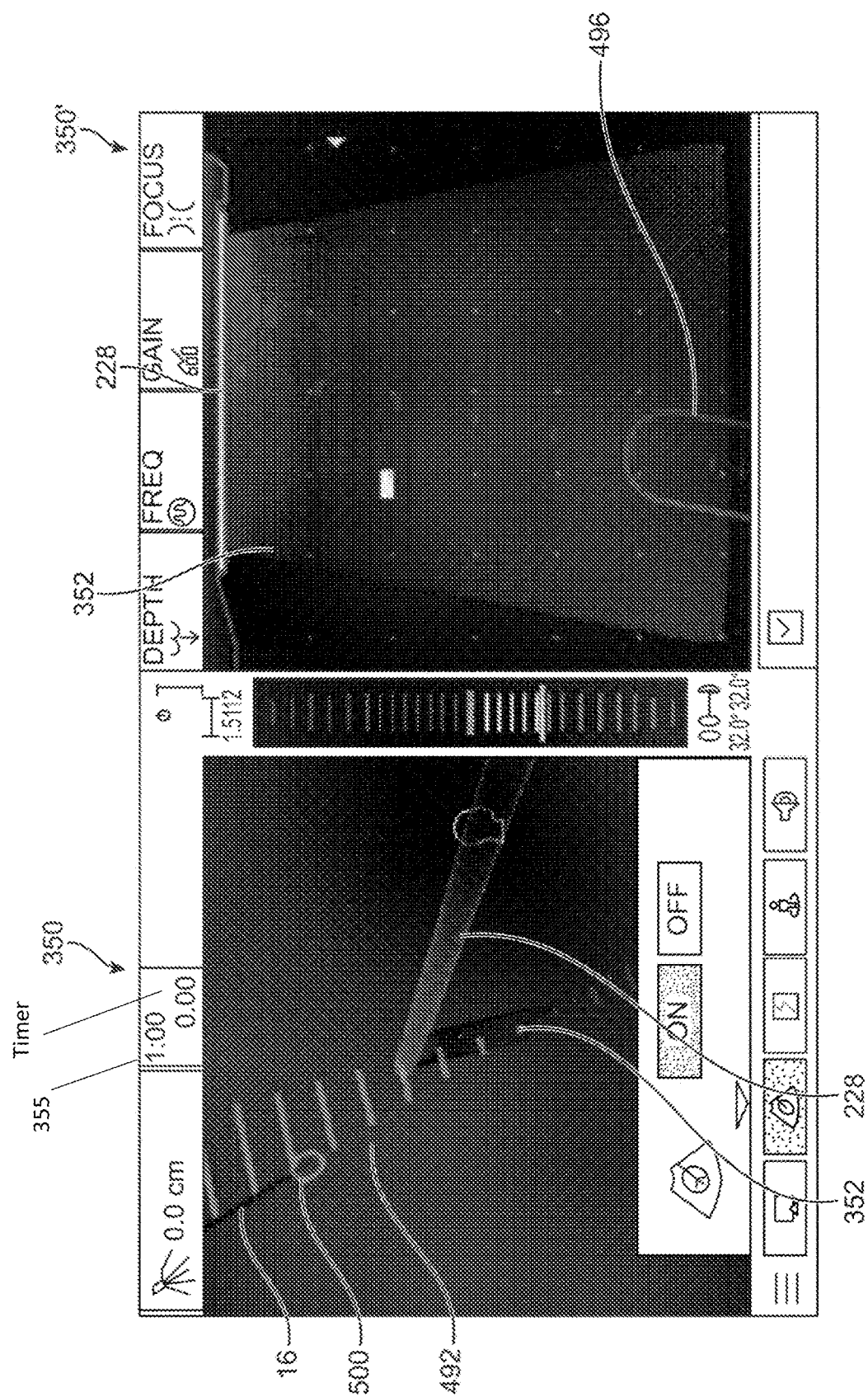

FIG. 8D shows another variation where the GUI 350, 350' may be configured to show a visual indicator of the expected ablation volume at the end of the treatment portion of the ablation device 16. The expected ablation volume may display an expected 3D ablation cage or treatment zone 500 as an indicator to the user as a 3D visual reference for physical dimensions to further assist in electrode array placement, as described in further detail below.

Additional details of the graphical user interfaces are described in further detail in U.S. patent application Ser. No. 13/069,472 (U.S. Pub. 2012/0245575) and Ser. No. 13/069,497 (U.S. Pub. 2012/0245576) both filed Mar. 23, 2011; and U.S. patent application Ser. No. 14/537,899 filed Nov. 10, 2014 (U.S. Pub. 2015/0190206), each of which is incorporated herein by reference in its entirety and for any purpose.

During use, when deploying the stylets 20 from the ablation device 16, a deployment length of the stylets 20 may be adjusted from any length of a partially extended configuration to a fully extended configuration. Depending upon the length of the deployed stylets 20 from the ablation device 16, the size of the ablation zone surrounding the stylets 20 will vary accordingly as well. Hence, the user may adjust the size of the ablation zone to match or correlate with the size of, e.g., a fibroid, as well as to minimize ablation of the tissue region surrounding the treated region.

To facilitate sizing of the treatment region, a visual representation of the ablation zone may be provided to the user so that the user may quickly confirm not only that the positioning of the ablation device 16 relative to the treatment area is sufficient but also that the deployment length of the stylets 20 is suitable for creating an ablation zone of sufficient size. Hence, a dynamic imaging system which automatically generates a visual representation of the ablation zone, based on specified parameters, may be provided.

An example is shown in the GUI 350 of FIGS. 9A to 9C which illustrate the graphic representation of the deployment of the stylets 20 and the ablation zone being sized accordingly in a visual representation. FIG. 9A shows an example of GUI 350 illustrating an image representative of the ultrasound probe 228 and the ablation device 16 in proximity to the probe 228 when inserted within the tissue region of interest for treatment.

The ultrasound probe 228 may be actuated to provide an ultrasound image 352 of the tissue region and the probe 228 may be rotated about its longitudinal axis to adjust the image 352 which may be displayed upon GUI 350. A corresponding computer display 220, as shown in FIG. 10A, may simultaneously present an image of the probe 228 and the ultrasound image 352 on a separate monitor or upon the same GUI 350 shown in FIG. 9A.

With the probe 228 and ablation device 16 positioned within or in proximity to the tissue region to be treated, the stylets 20 may be advanced through the corresponding openings 7 for deployment into the surrounding tissue region. As the stylets 20 are deployed, the effective ablation may change in a corresponding manner depending on the length of the deployed stylets 20. Hence, a boundary of the effective ablation zone may be illustrated as a three-dimensional border or cage or treatment zone 354 in the GUI 350 to provide the user a visual guide as to how large the ablation zone will be during treatment, as shown in FIG. 9B. As the stylets 20 are deployed, its deployment position or length may be tracked by the system (e.g., processor) so that the deployed length of the stylets 20 are known at any time. Based on the known length of the stylets 20, the ablation border or cage or treatment zone 354 may be calculated (e.g., by the processor) to automatically determine the size given that the treatment temperature is predetermined. The user may accordingly utilize the visual border or cage or treatment zone 354 in order to facilitate positioning of the ablation device 16 relative to the tissue region of interest for treatment. The border or cage or treatment zone 354 may be presented visually as an elliptical, ovoid, or spherical shape depending on the effective ablation zone.

Additionally, depending on the length of the stylets 20 deployed from their respective openings from the ablation device 16, the border or cage or treatment zone 354 may vary its size accordingly. An example is shown between FIGS. 9B and 9C which illustrate the stylets 20 deployed at a first configuration which is a partial deployed length of the stylets 20 and its corresponding border or cage 354. As shown in FIG. 9C, the stylets 20 may be deployed to a second configuration in which the stylets 20' have a fully deployed length and the border or cage or treatment zone 354' is shown as having a corresponding size which is relatively larger in size and volume than the border or cage or treatment zone 354 shown in FIG. 9B. Hence, depending on the length of the deployed stylets 20 from ablation device 16, the ablation border or cage or treatment zone 354 may be represented in the GUI 350 as having a corresponding size which may change in real time to facilitate treatment.

The ablation device 16 may be utilized in combination with the ultrasound probe 228 and as the probe 228 is rotated about its longitudinal axis to adjust the image 352, the corresponding border between the image 352 and ablation border or cage or treatment zone 354 may be represented in the GUI 350 as well. FIG. 9B illustrates the intersection 356 between the plane of the image 352 and the border or cage or treatment zone 354 and the system may project the intersection 356 on the image 352 displayed upon display 220 as shown correspondingly in FIG. 10B. As the stylets 20' are deployed and the size of its corresponding border or cage or treatment zone 354' changes in size, as indicated in FIG. 9C, the projected intersection 356' as shown in image 352 may also change its size correspondingly, as shown in FIG. 10C.

Because the probe 228 may be rotated about its longitudinal axis to adjust the image 352, the corresponding border between the image 352 and ablation border or cage or treatment zone 354 may also change in real time. FIGS. 11A to 11C illustrate one example of the deployed stylets 20 having a selected deployed length and its corresponding ablation border or cage or treatment zone 354 displayed upon the image 352. With the ablation device 16 maintained in its position, the probe 228 may be rotated about its longitudinal axis such that the projected image 352 sweeps about or rotates as well. Thus, the projected intersection 362 between the image 352 and border or cage 354 may change in real time from an initial intersection 362 to intersection 362' as shown in FIG. 11B, to intersection 362" as shown in FIG. 11C. The corresponding images of the intersection 362, 362', 362" may be shown upon the display 370 from FIGS. 12A to 12C which may be utilized by the user as a visual confirmation to ensure that the desired treatment region is entirely encompassed within the ablation zone.

The size of the ablation border or cage or treatment zone 354 graphically displayed to the user may be determined by the determination of the preset target temperature which is calculated, for example, by taking an average of the temperatures provided by the stylets 20, which may be displayed as the target time 355 on the GUI, as previously described herein. For example, for a desired target temperature of 95° C. provided by the deployed stylets 20, ablation settings with respect to the representative ablation size are provided in Table 1 which illustrates an expected ablation zone border or cage or treatment zone 354 in the representative ablation size for a given deployment length of the stylets 20 at a predetermined target time for treatment in order to achieve the expected target treatment temperature.

TABLE 1

Representative Ablation Settings.

| REPRESENTATIVE ABLATION SIZE | DEPLOYMENT | TARGET TIME | TARGET |
|---|---|---|---|
| 1.0 × 0.8 cm | 0.0 cm | 15 sec | 15 $W^2$ |
| 1.5 × 1.2 cm | 0.0 cm | 1 min | 15 $W^2$ |
| 1.9 × 1.7 cm | 0.5 cm | 1 min | 95° C. |
| 2.1 × 1.9 cm | 1.0 cm | 0.5 min | 95° C. |
| 2.7 × 2.3 cm | 1.5 cm | 2 min | 95° C. |
| 3.3 × 2.7 cm | 2.0 cm | 3 min | 95° C. |
| 3.9 × 3.0 cm | 2.5 cm | 4 min | 95° C. |
| 4.2 × 3.4 cm | 3.0 cm | 5.5 min | 95° C. |
| 4.8 × 3.7 cm | 3.5 cm | 7 min | 95° C. |
| 5.2 × 4.3 cm | 4.0 cm | 7.5 min | 95° C. |
| 5.6 × 4.4 cm | 4.5 cm | 8 min | 95° C. |
| 6.0 × 5.0 cm | 5.0 cm | 12 min | 95° C. |

Figure 13A:
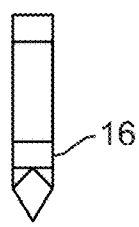
FIGS. 13A to 13C illustrate representative figures showing the length and width of the representative ablation size for the given deployment length of the stylets in the ablation border or cage.
Figure 13B:
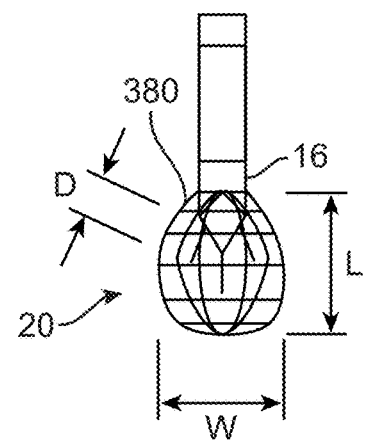
Figure 13C:
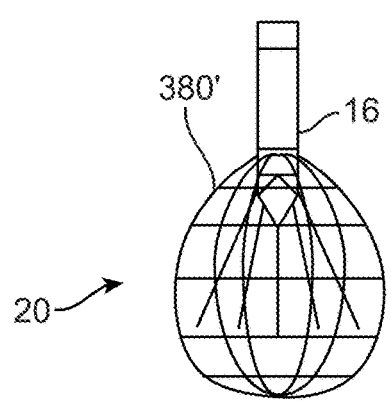

Hence, for a give stylet deployment length, the ablation border or cage may be illustrated in the GUI with the given dimensions shown above. FIGS. 13A to 13C illustrate representative figures showing the length L and width W of the representative ablation size for the given deployment length D of the stylets 20 in the ablation border or cage or treatment zone 380 in FIG. 13B and the correspondingly larger ablation border or cage 380' for the more fully deployed stylets 20 in FIG. 13C.

Figure 13D:
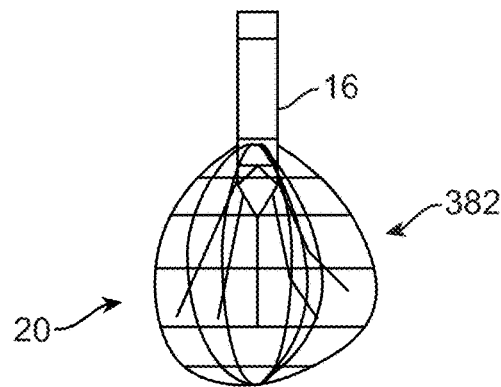
FIG. 13D illustrates an ablation device having one or more stylets which are deployed at an angle.

In another variation, if one or more of the stylets 20 were to exit from their respective openings in the ablation device at unexpected angles or unexpected deployment lengths, the system may generate a real-time image of the expected ablation border or cage to illustrate to the user what the actual ablation zone will be during treatment. This may be used as a check to the user to determine whether the stylets are properly deployed and positioned. An example is shown in FIG. 13D which illustrates an ablation device 16 having one or more stylets 20 which are deployed at an angle. The corresponding image of the ablation border or cage or treatment zone 382 may be seen as forming a non-uniform shape which may be indicative to the user of one or more an improperly deployed stylets. For this particular embodiment, each of the stylets may incorporate its own temperature sensor to provide real-time feedback for determining the size of the actual ablation zone.

It will be appreciated by those skilled in the art that changes can be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A system for visualizing a tissue treatment, comprising:
a tissue treatment instrument having one or more stylets that are deployable and a first energy sensor;
an ultrasound imaging instrument configured to generate an ultrasound imaging plane and further having a second energy sensor;
an energy field generator configured for placement in proximity to a patient body and further configured to generate an output indicative of a relative position between the first and second energy sensors; and
a console in communication with the tissue treatment instrument, the ultrasound imaging instrument, and the energy field generator,
wherein the console is configured to generate a representative image of the tissue treatment instrument oriented relative to the ultrasound imaging plane, and wherein the console is also configured to generate an image of an expected ablation border or expected treatment zone having a size that is based upon a deployment state of the one or more stylets after the one or more stylets are deployed;

wherein the console is configured to provide an output indicating a predetermined target time; and wherein the size of the expected ablation border or the expected treatment zone is based on the deployment state of the one or more stylets, the predetermined target time, and a predetermined target temperature.

2. The system of claim 1 wherein the tissue treatment instrument comprises an elongate body having the one or more stylets and a piercing distal tip.

3. The system of claim 2 wherein the tissue treatment instrument comprises an ablation instrument.

4. The system of claim 1 wherein the tissue treatment instrument is configured to impart ablation energy, cryoablation energy, plasma energy, or mechanical energy.

5. The system of claim 1 wherein the energy field generator comprises an electromagnetic field generator.

6. The system of claim 1 wherein the energy field generator is configured to impart radio frequency energy, microwave energy, ultrasound energy, or infrared energy.

7. The system of claim 1 wherein the ultrasound imaging instrument comprises an elongate ultrasound probe and a sleeve having the second energy sensor.

8. The system of claim 1 wherein the energy field generator is configured for placement in proximity to a pelvis of the patient body.

9. The system of claim 1 wherein the console comprises a computer.

10. The system of claim 1 wherein the console is configured to determine the expected ablation border or the expected treatment zone in real time during deployment of the one or more stylets.

11. The system of claim 1, wherein the console is configured to provide (1) the image of the expected ablation border or the expected treatment zone, and (2) the output indicating the predetermined target time, for simultaneous presentation to a user of the system.

12. A method of visualizing a tissue treatment, comprising:

receiving a first input from a tissue treatment instrument having one or more stylets that are deployable and a first energy sensor;

receiving a second input from an ultrasound imaging instrument configured to generate an ultrasound imaging plane and further having a second energy sensor;

displaying a position of the tissue treatment instrument relative to the ultrasound imaging instrument based upon an output received from an energy field generator placed in proximity to a patient body, wherein the output is indicative of a relative position between the first and second energy sensors; and displaying a representative image of an expected ablation border or expected treatment zone having a size that is based upon a deployment state of the one or more stylets after the one or more stylets are deployed;

wherein the method further comprises displaying an indication of a predetermined target time; and wherein the size of the expected ablation border or the expected treatment zone is based on the deployment state of the one or more stylets, the predetermined target time, and a predetermined target temperature.

13. The system of claim 1, wherein the predetermined target temperature is 95° C.

14. The system of claim 1, wherein the console is configured to provide a timer for simultaneous display with the output indicating the predetermined target time.

15. The method of claim 12, wherein the indication of the predetermined target time is displayed simultaneously with the image of the expected ablation border or the expected treatment zone.

16. The method of claim 12 wherein the tissue treatment instrument comprises an ablation instrument.

17. The method of claim 12 wherein the tissue treatment instrument is configured to impart ablation energy, cryoablation energy, plasma energy, or mechanical energy.

18. The method of claim 12 wherein the energy field generator comprises an electromagnetic field generator.

19. The method of claim 12 wherein the energy field generator is configured to impart radio frequency energy, microwave energy, ultrasound energy, or infrared energy.

20. The method of claim 12 wherein the act of receiving the second input comprises receiving the second input from an elongate ultrasound probe and sleeve having the second energy sensor.

21. The method of claim 12 wherein the first input and second input are received in a console coupled to the tissue treatment instrument, the ultrasound imaging instrument, and the energy field generator.

22. The method of claim 21 wherein the act of displaying comprises displaying the position via a monitor coupled to the console.

23. The method of claim 21 wherein the energy field generator is configured for placement in proximity to a pelvis of the patient body.

24. The method of claim 12 wherein the act of displaying the representative image of the expected ablation border or the expected treatment zone comprises displaying the expected ablation border or the expected treatment zone in real time during deployment of the one or more stylets.

25. The method of claim 12, wherein the predetermined target temperature is 95° C.

26. The method of claim 12, further comprising displaying a timer simultaneously with the indication of the predetermined target time.

* * * * *